US010100014B2

(12) United States Patent
Newkome et al.

(10) Patent No.: US 10,100,014 B2
(45) Date of Patent: Oct. 16, 2018

(54) METALLOTRIANGLE-BASED NANOMOLECULES AND METHODS OF MAKING THE SAME

(71) Applicants: George R. Newkome, Medina, OH (US); Charles N. Moorefield, Akron, OH (US)

(72) Inventors: George R. Newkome, Medina, OH (US); Charles N. Moorefield, Akron, OH (US)

(73) Assignee: The University of Akron, Akron, OH (US)

( * ) Notice: Subject to any disclaimer, the term of this patent is extended or adjusted under 35 U.S.C. 154(b) by 62 days.

(21) Appl. No.: 15/007,456

(22) Filed: Jan. 27, 2016

(65) Prior Publication Data
US 2016/0214938 A1 Jul. 28, 2016

Related U.S. Application Data

(60) Provisional application No. 62/108,195, filed on Jan. 27, 2015.

(51) Int. Cl.
*C07D 213/22* (2006.01)

(52) U.S. Cl.
CPC .................. *C07D 213/22* (2013.01)

(58) Field of Classification Search
None
See application file for complete search history.

(56) References Cited

U.S. PATENT DOCUMENTS

| 6,399,717 B1 | 6/2002 | Newkome | |
| 8,227,614 B2 | 7/2012 | Newkome | |
| 2009/0131656 A1* | 5/2009 | Newkome | C07F 15/025 540/465 |

OTHER PUBLICATIONS

Sarkar, et al., Angew. Chemie. Int. Ed., 53:12182. (Year: 2014).*
Moorefield, et al., Brazilian J. Pharm. Sci., 49:67. (Year: 2013).*
Richardson, Lewis F., "Atmospheric Diffusion Shown on a Distance-Neighbor Graph" Proceedings of the Royal Society of London. Series A, Containing Papers of a Mathematical and Physical Character, 110(756), pp. 709-737 (Nov. 7, 1925).
Roush, et al. "Micelles. Part 1. Cascade molecules: a new approach to micelles. A [27]-arborol", The Journal of Organic Chemistry, 50(11), pp. 2003-2004 (1985).
Newkome, et al. "Dendrimers Derived from 1-->3 Branching Motifs" Chem. Rev. 110, pp. 6338-6442 (2010).
Sugiura, et al. "A Mandala-Patterned Bandanna-Shaped Porphyrin Oligomer, $C_< 1244>$ $H_< 1350>$ $N_< 84>$ $Ni_< 20>$ $O_< 88>$, Having a Unique Size and Geometry" Chemistry letters, 11, pp. 1193-1194 (1999).
Newkome, et al. "Nanoassembly of a Fractal Polymer: A Molecular 'Sierpinski Hexagonal Gasket'" Science, vol. 312, pp. 1782-1784 (Jun. 23, 2006).
Hwang, et al. "Construction of Triangular Metallomacrocyles: [M3(1,2-bis(2,2':6',2"-terpyridin-4-yl-ethynyl)benzene)2] [M=Ru(II), Fe(II), 2Ru(II)Fe(II)]" Chem. Commun., pp. 713-715 (2005).
Saha, et al. "Dynamic heteroleptic metal-phenanthroline complexes: from structure to function" Dalton Trans., vol. 43, pp. 3815-3834 (2014).
Sommer, et al. "Supramolecular Chemistry: Molecular Recognition and Self-Assembly Using Rigid Spacer-Chelators Bearing Cofacial Terpyridyl Palladium(II) Complexes Separated by 7 Angstroms" J. Am. Chem. Soc. vol. 123, pp. 3940-3952 (2001).
Constable, et al. "2,2':6,2"-Terpyridine-4'(1'H)-thione: a missing link in metallosupramolecular chemistry" New J. Chem., vol. 29, pp. 1475-1481 (2005).
Hwang, et al. "Design, self-assembly, and photophysical properties of pentameric metallomacrocycles: [M5(N-hexyl[1,2-bis(2,2':6',2"-terpyridin-4-y1)]carbazole)5][M=Fe(II), Ru(II), and Zn(II)]" Chem. Commun., pp. 4672-4674 (2005).
Newkome, et al. "Self- and Directed Assembly of Hexaruthenium Macrocycles" Angew. Chem. Ind. Ed., vol. 38, No. 24, pp. 3717-3721 (1999).
Perera, et al. "Sterically congested, hexameric tetrakispyridinyl-PdII/CdII-metallomacrocycles: self-assembly and structural characterization" Chem. Commun., vol. 47, pp. 4658-4660 (2011).
Chan, et al. "Design, Synthesis, and Traveling Wave Ion Mobility Mass Spectrometry Characterization of Iron(II)—and Ruthenium(II)—Terpyridine Metallomacrocycles" J. Am. Chem. Soc. vol. 133, pp. 11967-11976 (2011).
Chan, et al. "Towards Larger Polygonal Architectures: Synthesis and Characterization of Iron(II)—and Ruthenium(II)—Bis(terpyndine) Metallomacrocyles" Chem. Eur. J., vol. 17, pp. 7750-7754 (2011).
Chan, et al. "Self-Assembly and Traveling Wave Ion Mobility Mass Spectrometry Analysis of Hexacadmium Macrocyles" J. Am. Chem. Soc., vol. 131, pp. 16395-16397 (2009).
Andres, et al. "Metallo-Polymerization/-Cyclization of a C16-Bridged Di-Terpyridine Ligand and Iron(II) Ions" Macromol. Rapid Commun., vol. 25, pp. 1371-1375 (2004).
Constable, et al. "When is a metallopolymer not a metallopolymer? When it is a metallomacrocycle" Dalton Trans., vol. 40, pp. 1524-1534 (2011).
Wang, et al. "Stoichiometric Self-Assembly of Shape-Persistent 2D Complexes: A Facile Route to a Symmetric Supramolecular Spoked Wheel" J. Am. Chem. Soc. vol. 133, pp. 11450-11453 (2011).
Schultz, et al. "Stoichiometric Self-Assembly of Isomeric, Shape-Persistent, Supramolecular Bowtie and Butterfly Structures" J. Am. Chem. Soc. vol. 134, pp. 7672-7675 (2012).

(Continued)

*Primary Examiner* — Michael P Barker
(74) *Attorney, Agent, or Firm* — Renner, Kenner, Greive, Babak, Taylor & Weber

(57) ABSTRACT

Metallotriangle-based nanomolecules are formed by a one-step self-assembly of specifically chosen shaped poly-ligand monomers, the poly-ligand monomers coordinating with metal ions through coordinating ligands. The poly-ligand monomers are defined by vertex groups having arms extending therefrom and ending in coordinating ligands. Based on the desired metallotriangle-based nanomolecule structure to be assembled, specifically shaped poly-ligand monomers and metal ions are chosen and mixed in appropriate ratios so that coordinating ligands bind to metal ions and the poly-ligand monomers thus spontaneously self-assemble into the desired metallotriangle-based nanomolecule structure.

26 Claims, 15 Drawing Sheets

(56) References Cited

OTHER PUBLICATIONS

Lu, et al. "From supramolecular triangle to heteroleptic rhombus: a simple bridge can make a difference" Chem. Commun., vol. 48, pp. 9873-9875 (2012).

Jarosz, et al. "Platinum(II) Terpyridyl-Acetylide Dyads and Triads with Nitrophenyl Acceptors via a Convenient Synthesis of a Boronated Phenylterpyridine" Inorg. Chem. vol. 48, pp. 2420-2428 (2009).

Hoaglund-Hyzer, et al. "Anhydrous Protein Ions" Chem. Rev. vol. 99, pp. 3037-3079 (1999).

Trimpin, et al. "Resolving Oligomers from Fully Grown Polymers with IMS-MS" Anal. Chem., vol. 79, pp. 7965-7974 (2007).

Hilton, et al. "Structural Analysis of Synthetic Polymer Mixtures Using Ion Mobility and Tandem Mass Spectrometry" Anal. Chem. vol. 80, pp. 9720-9725 (2008).

Sun, et al. "On-Surface construction of a metal-organic Sierpinski Triangle" Chem. Commun., vol. 51, pp. 14164-14166 (2015).

Nieckarz, et al. "Simulation of the self-assembly of simple molecular bricks into Sierpinski triangles" Chem. Commun., vol. 50, pp. 6843-6845 (2014).

Nieckarz, et al. "Understanding Pattern Formation in 2D Metal-Organic Coordination Systems on Solid Surfaces" J. Phys. Chem., vol. 117, pp. 11229-11241 (2013).

Shang, et al., "Assembling Molecular Sierpinski Triangle Fractals" Abstract only, Nature Chemistry, vol. 7, Issue 5, pp. 389-393 (2015).

Zhang, et al. "Controlling Molecular Growth Between Fractals and Crystals on Surfaces" ACS Nano, vol. 9, No. 12, pp. 11909-11915 (2015).

Shang, et al. "Assembling molecular Sierpinski Triangle Fractals" Nature Chemistry, vol. 7, pp. 389-393 (May 2015).

\* cited by examiner

METALLOTRIANGLE-BASED NANOMOLECULES AND METHODS OF MAKING THE SAME

CROSS-REFERENCE TO RELATED APPLICATIONS

This application claims the benefits of U.S. Provisional Patent Application No. 62/108,195, filed Jan. 27, 2015 incorporated herein by reference.

STATEMENT REGARDING FEDERALLY SPONSORED RESEARCH OR DEVELOPMENT

This invention was made with government support under CHE-1151991 & CHE-1308307 awarded by the National Science Foundation. The government has certain rights in the invention.

FIELD OF THE INVENTION

The present invention generally resides in the field of precision nanomolecules and nano scale processes involving the manipulation of individual molecules to create metallotriangle-based molecular architectures. The present invention also resides in the art of coordination chemistry, employing metal ions and associated coordinating ligands.

BACKGROUND OF THE INVENTION

Macromolecular construction has evolved to include utilitarian composite materials whereby interdependent components are precisely matched for desired physicochemical properties. Targeted materials and properties, derived from minimum-assembly protocols, are desirable due to a variety of considerations, including economic viability, ease of construction, and enhanced scale-up potential. Thus, supramolecular and iterative-based chemistries converge in rational fractal designs; whereby, molecular architectures exhibit self-similarity on differing scales to provide a balance of interrelated attributes and structural components. Research efforts in our laboratories suggest that fundamental supramacronmolecular properties can be affected by subtle changes in design parameters.

The use of ligand-metal-ligand connectivity has served to expand the directed and self-assembly work into the novel, utilitarian "fractal" macro- and nanomolecular architecture arena. These constructs have led to the development of materials with demonstrated potential as energy storage and release devices based on stable oxidized and reduced metal states, as components of molecular devices, such as in new photovoltaic cells and organic light emitting diodes (OLEDs), based on their photo- and electroluminescence properties, and as molecular switches, foundations for information storage and retrieval, and optical display components, based on their low spin-high spin characteristics predicated on the light-induced excited spin-state trap (LIESST) effect.

The past several years have witnessed increased interest in the general topic of metallo-fractal materials, particularly in relation to their future nanotechnological applications. These directions have been built on the melding of classical synthetic strategies with materials science construction and characterization protocols to "tune" bulk and localized supramolecular properties to specific tasks, and to assemble macromolecular infrastructures capable of functioning alone or in concert within materials at composite interfaces.

Considering the constant quest for new monomers, the ability to incorporate specifically directed metal centers, and structural components that can facilitate access to application-oriented architectures, as well as innovative construction protocols, we herein demonstrate the construction of new nanomolecules predicated on: (1) the self-assembly of fractal-based materials to allow access to network-based architectures utilizing new materials and composites with enhanced functional properties; (2) ametal-ligand assembly employing preconstructed synthons to facilitate the generation of nano- and macroscopic, precisely positioned, dual and polymetal arrays giving rise to new multicomponent macromolecular systems; and (3) targeted assembly of ordered aggregates of fractal-based architectures possessing polymetallic subunits that facilitate the selective construction of a desired pattern out of the many different network patterns.

SUMMARY OF THE INVENTION

In a first embodiment, the present invention provides a method of preparing a metallotriangle-based nanomolecule. The method comprising the steps of: mixing a plurality of poly-ligand monomers with a plurality of metal ions, the poly-ligand monomers being selected from the group consisting of V-, wide V-, X-, symmetric Y-, unsymmetrical Y-, K-, W-, hex-star-, penta-star-, and I-shaped monomers wherein: (a) the V-shaped monomers include a cyclic V-vertex group with first and second coordinating V-arms extending from the cyclic V-vertex group at 60° from one another, each of the first and second coordinating V-arms terminating in a metal-coordinating V-ligand (b) the wide V-shaped a cyclic wide V-vertex group with first and second coordinating wide V-arms extending from the cyclic wide V-vertex group at 120° from one another, each of the first and second coordinating wide V-arms terminating in a metal-coordinating wide V-ligand (c) the X-shaped monomers include a cyclic X-vertex group with first and second coordinating X-arms extending from the cyclic X-vertex group at 60° from one another, and opposed third and fourth coordinating X-arms extending from the cyclic X-vertex group at 60° from one another in a direction opposite to the first and second coordinating X-arms, each of the first, second, third, and fourth coordinating X-arms terminating in a metal-coordinating X-ligand; (d) the unsymmetrical Y-shaped monomers include a cyclic unsymmetrical Y-vertex group with first and second coordinating unsymmetrical Y-arms extending from the cyclic unsymmetrical Y-vertex group at 180° from one another, and a third coordinating unsymmetrical Y-arm extending at 120° from the second coordinating unsymmetrical Y-arm, each of the first, second, and third coordinating unsymmetrical Y-arms terminating in a metal-coordinating unsymmetrical Y-ligand; (e) the symmetric Y-shaped monomers include a cyclic symmetric Y-vertex group with first, second, and third coordinating symmetric Y-arms extending from the cyclic symmetric Y-vertex group at 120° intervals, each of the first, second, and third coordinating symmetric Y-arms terminating in a metal-coordinating symmetric Y-ligand; (f) the K-shaped monomers include a cyclic K-vertex group with first and second coordinating K-arms extending from the cyclic K-vertex group at 180° from one another, a third coordinating K-arm extending from the cyclic K-vertex group at 60° from the first coordinating K-arm and at 120 from the second coordinating K-arm, and a fourth coordinating K-arm extending from the cyclic K-vertex group at 60° from the second coordinating K-arm and at 120 from the first coordinating K-arm, the third and fourth coordinating K-arms extending from the cyclic K-vertex group at 60 from one another, each of the first, second, third, and fourth coordinating K-arms terminating in a metal-coordinating K-ligand; (g) the W-shaped monomers include a cyclic W-vertex group with a first coordinating W-arm and a second coordinating W-arm extending from the cyclic W-vertex group at 60° from one another, and a third coordinating W-arm extending at 60° from the second coordinating W-arm and 120° from the first coordinating W-arm, each of the first, second, and third coordinating W-arms terminating in a metal-coordinating unsymmetrical W-ligand; (h) the hex-star-shaped monomers include a cyclic hex-star-vertex group having six coordinating hex-star-arms extending from the cyclic hex-star-vertex group at 60° intervals and each terminating in a metal-coordinating hex-star-ligand; (i) the penta-star-shaped monomers include cyclic penta-star-vertex group having 5 coordinating penta-star-arms extending from the cyclic penta-star-vertex group at 60° intervals and each terminating in a metal-coordinating hex-star-ligand; and (j) the 1-shaped monomers include a cyclic I-vertex group with first and second coordinating I-arms extending from the cyclic I-vertex group at 180° from one another, each I-arm terminating in a metal-coordinating I-ligand; and wherein: the number and type of poly-ligand monomers and the number of metal ions are chosen and mixed in stoichiometric ratios such that, after the step of mixing, the metallotriangle-based nanomolecule self-assembles through the coordination of all of the metal coordinating V-, wide V-, X-, symmetric Y-, unsymmetrical Y-, K-, W-, hex-star-, penta-star-, and I-ligands of the plurality of poly-ligand monomers with the plurality of metal ions.

In a second embodiment, the present invention provides a method of preparing a metallotriangle-based nanomolecule as in the first embodiment, wherein the metal coordinating V-, wide V-, X-, symmetric Y-, unsymmetrical Y-, K-, W-, hex-star-, penta-star-, and I-ligands are selected from the group consisting of monodentate ligands, bidentate ligands, and tridentate ligands.

In a third embodiment, the present invention provides a method of preparing a metallotriangle-based nanomolecule as in either the first or second embodiment, wherein each of the metal coordinating V-, wide V-, X-, symmetric Y-, unsymmetrical Y-, K-, W-, hex-star-, penta-star-, and I-ligands is a tridentate ligand.

In a fourth embodiment, the present invention provides a method of preparing a metallotriangle-based nanomolecule as in any of the first through third embodiments, wherein two of the tridentate ligands coordinate with one of the plurality of metal ions to bind 6 atoms thereto.

In a fifth embodiment, the present invention provides a method of preparing a metallotriangle-based nanomolecule as in any of the first through fourth embodiments, wherein the metal coordinating V-, wide V-, X-, symmetric Y-, unsymmetrical Y-, K-, W-, hex-star-, penta-star-, and I-ligands are selected from substituted 4'-attached [to the directed monomer unit(s)]-terpyridines, 4-substituted pyridines and aryl carboxylates.

In a sixth embodiment, the present invention provides a method of preparing a metallotriangle-based nanomolecule as in any of the first through fifth embodiments, wherein at least two of the metal coordinating V-, wide V-, X-, symmetric Y-, unsymmetrical Y-, K-, W-, hex-star-, penta-star-, and I-ligands are tridentate ligands and at least two of those tridentate ligands coordinate with a given metal ion.

In a seventh embodiment, the present invention provides a method of preparing a metallotriangle-based nanomolecule as in any of the first through sixth embodiments, wherein the metal coordinating V-, wide V-, X-, symmetric Y-, unsymmetrical Y-, K-, W-, hex-star-, penta-star-, and T-ligands are selected from pyridines, bipyridines, terpyridines, pyrroles, polypyrroles, thiophenes, polythiophenes, phosphines, polyphosphines, isoxazoles, oxazoles, pyrimidines, polypyrimidines, pyridazines, poly pyridazines, polyoxazoles, thiazoles, and polythiazoles.

In an eighth embodiment, the present invention provides a method of preparing a metallotriangle-based nanomolecule as in any of the first through seventh embodiments, wherein the metal coordinating V-, wide V-, X-, symmetric Y-, unsymmetrical Y-, K-, W-, hex-star-, penta-star-, and I-ligands pyridines, bipyridines, terpyridines.

In a ninth embodiment, the present invention provides a method of preparing a metallotriangle-based nanomolecule as in any of the first through eighth embodiments, wherein the cyclic V-, wide V-, X-, symmetric Y-, unsymmetrical Y-, K-, W-, hex-star-, penta-star-, and I-vertex groups are selected from aromatic rings with 6 atoms in the ring structure.

In a tenth embodiment, the present invention provides a method of preparing a metallotriangle-based nanomolecule as in any of the first through ninth embodiments, wherein the cyclic V-, wide V-, X-, symmetric Y-, unsymmetrical Y-, K-, W-, hex-star-, penta-star-, and I-vertex groups are selected from phenyl groups, naphthalene groups, polyarylenes and heteroaromatic, polyheteroaromatic, rigid cycloalkanes and cholesteric.

In an eleventh embodiment, the present invention provides a method of preparing a metallotriangle-based nanomolecule as in any of the first through tenth embodiments, wherein the cyclic V-, wide V-, X-, symmetric Y-, unsymmetrical Y-, K-, W-, hex-star-, penta-star-, and I-vertex groups are all phenyl groups.

In a twelfth embodiment, the present invention provides a method of preparing a metallotriangle-based nanomolecule as in any of the first through eleventh embodiments, wherein the coordinating V-, wide V-, X-, symmetric Y-, unsymmetrical Y-, K-, W-, hex-star-, penta-star-, and I-arms are defined by a spacer group between a respective cyclic V-, wide V-, X-, symmetric Y-, unsymmetrical Y-, K-, W-, hex-star-, penta-star-, and I-vertex group and an associated metal coordinating V-, wide V-, X-, symmetric Y-, unsymmetrical Y-, K-, W-, hex-star-, penta-star-, and I-ligand.

In a thirteenth embodiment, the present invention provides a method of preparing a metallotriangle-based nanomolecule as in any of the first through twelfth embodiments, wherein the at least one spacer group is selected from phenyl, biphenyl, p-terphenyl, polyarylenes and heteroaromatic, polyheteroaromatic, rigid cycloalkanes, cholesteric, and alkyne, aralkyne, diazo and polydiazo groups.

In a fourteenth embodiment, the present invention provides a method of preparing a metallotriangle-based nanomolecule as in any of the first through thirteenth embodiments, wherein the step of mixing includes combining the poly-ligand monomers and metal ions in a solvent.

In a fifteenth embodiment, the present invention provides a method of preparing a metallotriangle-based nanomolecule as in any of the first through fourteenth embodiments, where the solvent is selected most commercial organic solvents.

In a sixteenth embodiment, the present invention provides a method of preparing a metallotriangle-based nanomolecule as in any of the first through fifteenth embodiments, where the solvent is selected from alcohols, aromatics, alkanes, alkenes, halocarbons, polar protic, polar aprotic and nonpolar liquids.

In a seventeenth embodiment, the present invention provides a method of preparing a metallotriangle-based nanomolecule as in any of the first through sixteenth embodiments, where the solvent is selected from MeOH and CHCl3, CH2Cl2, toluene, benzene, and ethylene gly col.

In an eighteenth embodiment, the present invention provides a method of preparing a metallotriangle-based nanomolecule as in any of the first through seventeenth embodiments, where the step of mixing further includes adding counter ions, wherein the metal ions and the counter ions form metal ion-counter ion pairs soluble in the step of mixing.

In a nineteenth embodiment, the present invention provides a method of preparing a metallotriangle-based nanomolecule as in any of the first through eighteenth embodiments, where the metal ions have a counter ion selected from Br—, I$^-$, ClO4$^-$, PF6$^-$, PF4$^-$, carboxylic acids, polycarboxylic acids, triflate, bis[2,2':6',2"]terpyridine-(CO2$^-$)n, and dendrimers with surface carboxylates.

In a twentieth embodiment, the present invention provides a method of preparing a metallotriangle-based nanomolecule as in any of the first through nineteenth embodiments, where the poly-ligand monomers are coordinated to a metal ion with an oxidation state of +2.

In a twenty-first embodiment, the present invention provides a method of preparing a metallotriangle-based nanomolecule as in any of the first through twentieth embodiments, where the metal ions are selected from the group consisting of Fe+2, Ru+2, Os+2, Ir+2, Zn+2, Cn+2, Cu+2, Ni+2, Ba+2, Mg+2, Mn+2, Cu+2, Pb+2, Ca+2, Cd+2, and combinations thereof.

In a twenty-second embodiment, the present invention provides a method of preparing a metallotriangle-based nanomolecule as in any of the first through twenty-first embodiments, where the metal ion is selected from the group consisting of Zn+2, Cn+2, Cu+2, Ni+2, Ba+2, Mg+2, Mn+2, Cu+2, Pb+2, Ca+2, Cd+2 and combinations thereof.

In a twenty-third embodiment, the present invention provides a method of preparing a metallotriangle-based nanomolecule as in any of the first through twenty-second embodiments, where the metal ion is selected from the group consisting of Fe$^{+2}$, Ru$^{+2}$, Os$^{+2}$, Ir$^{+2}$, Zn$^{+2}$, Cd$^{+2}$ and combinations thereof.

In a twenty-fourth embodiment, the present invention provides a method of preparing a metallotriangle-based nanomolecule as in any of the first through twenty-third embodiments, where sides of the metallotriangle-based nanomolecule are defined at least in part by two of the coordinating V-, X-, Y-, K-, star-, and I-arms bound to one metal ion.

In a twenty-fifth embodiment, the present invention provides a method of preparing a metallotriangle-based nanomolecule as in any of the first through twenty-fourth embodiments, where the poly-ligand monomers include a functional group in addition to the ligand groups.

In a twenty-sixth embodiment, the present invention provides a method of preparing a metallotriangle-based nanomolecule as in any of the first through twenty-fifth embodiments, where, in the step of mixing, each poly-ligand monomer of a particular shape is identical to the other poly-ligand monomers of that shape.

DETAILED DESCRIPTION OF ILLUSTRATIVE EMBODIMENTS

Figures 1A, 1B:
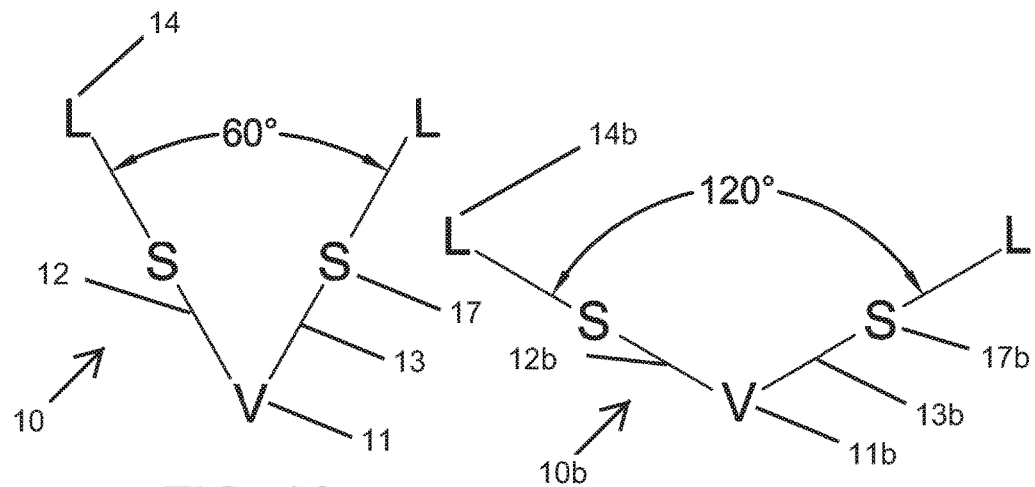
FIG. 1A is an exemplary schematic of a V-shaped monomer that may be employed to create metallotriangle-based nanomolecules in accordance with this invention.
FIG. 1B is an exemplary schematic of a wide V-shaped monomer that may be employed to create metallotriangle-based nanomolecules in accordance with this invention

The present invention provides metallotriangle-based nanomacromolecules and methods for making them. The term "metallotriangle-based" is to be understood as referring to the characteristic of including coordinating metals ("metallo") and having triangular or triangle-based overall structure or substructure(s) or both. The term "triangle-based" as used herein can include incomplete triangle substructures having two sides only, or diamond substructures that can generally be conceived of as two incomplete triangle substructures joined together. This understanding will be further clarified with reference to the above descriptions in analyzing exemplary nanomacromolecules disclosed herein.

The metallotriangle-based nanomolecules are formed by a one-step self-assembly of specifically chosen poly-ligand monomers, the poly-ligand monomers coordinating with metal ions through coordinating ligands. The poly-ligand monomers are defined by vertex groups having arms extending therefrom and ending in coordinating ligands. Based on the desired metallotriangle-based nanomolecule structure to be assembled, specifically shaped poly-ligand monomers and metal ions are chosen and mixed in appropriate ratios so that coordinating ligands bind to metal ions and the poly-ligand monomers thus spontaneously self-assemble into the desired metallotriangle-based nanomolecule structure.

In some embodiments, the specifically shaped poly-ligand monomers and metal ions are chosen and mixed in appropriate ratios so that coordinating ligands bind to metal ions and the poly-ligand monomers thus self-assemble into the desired metallotriangle-based nanomolecular structure in quantitative yields. In some embodiments, the metallotriangle-based nanomacromolecule structure is predictable based on the chosen poly-ligand monomers and ratios of the poly-ligand monomers and metal ions. In some embodiments, all coordinating ligands coordinate with a metal ion.

The poly-ligand monomers have many common features, but to help distinguish such features, each is identified by the particular type of poly-ligand monomer with which it is associated. It will be seen that V-, wide V-, X-, symmetric Y-, unsymmetrical Y-, K-, W-, hex-star-, penta-star-, and I-shaped monomers form the select group of poly-ligand monomers, and elements thereof are thus distinguished by modification by the use of "V", "wide V", "X", "symmetric Y", "unsymmetrical Y", "K", "W", "hex-star", "penta-star", and "I" designations. These poly-ligand monomers are shape-persistent. For simplicity and discussion purposes, the benzene ring is employed to provide specific examples of shape-persistent monomers and help define this directivity, but it is noted that any other six-membered ring can be utilized or fused rung system or heterocyclic ring system can be used equally well as long as rigidity is maintained. To appreciate the breadth of this invention, general schematics of the monomer structures are also provided without specific regard to compositional make-up.

The poly-ligand monomers are selected from V-shaped monomers, wide-V-shaped monomers, X-shaped monomers, symmetric Y-shaped monomers, unsymmetrical Y-shaped monomers, K-shaped monomers, W-shaped monomers, hex-star-shaped monomers, penta-star-shaped monomers, and I-shaped monomers.

With reference to FIG. 1A, a V-shaped monomer 10 includes a cyclic V-vertex group 11 with a first coordinating V-arm 12 and a second coordinating V-arm 13 extending from the cyclic V-vertex group 11 at 60° from one another, each of the first and second coordinating V-arms 12, 13 terminating in a metal-coordinating V-ligand 14. In some embodiments, the coordinating V-arms 12, 13 include a spacer group 17 between the cyclic V-vertex group 11 and the metal coordinating ligands 14.

A specific exemplary V-shaped monomer is provided below:

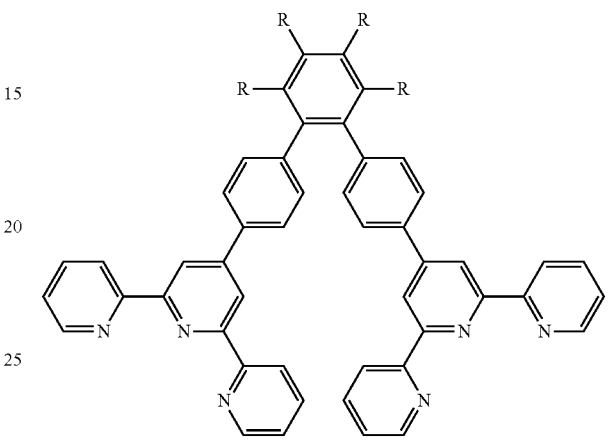

where the R's represent H, alkyl, aryl, alkoxyl, aryloxy, aralkyl, aralkyl-oxy, or any other similar substituent(s), including but not limited to heteroatoms (e.g., O, P, N, S) in said position. This is best envisioned as disubstitution from the 1,2-directivity of 1,2-benzene or the ortho positions which possess a precise 60° directionally.

With reference to FIG. 1B, a wide-V-shaped monomer 10b includes a cyclic wide-V-vertex group 11b with a first coordinating wide-V-arm 12b and a second coordinating wide-V-arm 13b extending from the cyclic wide-V-vertex group 11b at 120° from one another, each of the first and second coordinating wide-V-arms 12b, 13b terminating in a metal-coordinating in a metal-coordinating wide-V-ligand 14b. In some embodiments, the coordinating wide-V-arms 12b, 13b include a spacer group 17b between the cyclic wide-V-vertex group 11b and the metal coordinating ligands 14b.

A specific exemplary wide V-shaped monomer is provided below

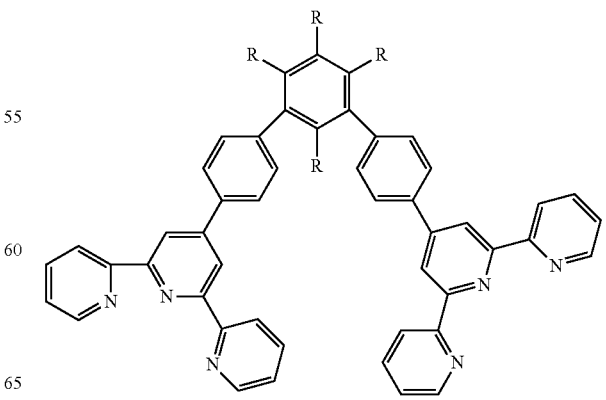

where the R's represent H, alkyl, aryl, alkoxyl, aryloxy, aralkyl, aralkyl-oxy, or any other similar substituent(s), including but not limited to heteroatoms (e.g., O, P, N, S) in said position. This is best envisioned as disubstitution from the 1,3-directivity of 1,3-benzene or the meta positions which possess a precise 120° directionality.

Figure 2:
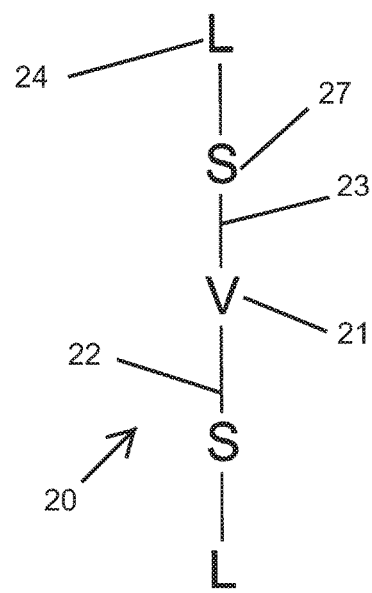
FIG. 2 is an exemplary schematic of a I-shaped monomer that may be employed to create metallotriangle-based nanomolecules in accordance with this invention.

With reference to FIG. 2, an I-shaped monomer 20 includes include a cyclic I-vertex group 21 with a first coordinating I-arm 22 and a second coordinating I-arm 23 extending from the cyclic I-vertex group 21 at 180° from one another, each I-arm 22, 23 terminating in a metal-coordinating I-ligand 24. In some embodiments, the coordinating I-arms 22, 223 include a spacer group 27 between the cyclic I-vertex group 21 and the metal coordinating ligands 24. It will be appreciated that the cyclic vertex group 21 is not specifically a vertex, as it does not define and angular point, but the term "vertex" is used to be consistent with the terminology used for the similar structures of the other shaped monomers.

A specific exemplary I-shaped monomer is provided below:

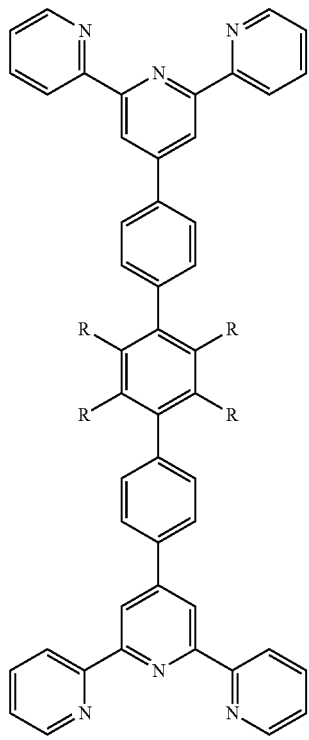

where the R's represent H, alkyl, aryl, alkoxyl, aryloxy, aralkyl, aralkyl-oxy, or any other similar substituent(s), including but not limited to heteroatoms (e.g., O, P, N, S) in said position. This is best envisioned as disubstitution from the 1,4-directivity of 1,4-benzene or the para positions which possess a precise 180° directionality. These "I" directed are used predominately to extend the length between the branching centers in order to maintain a precise linear motif.

Figure 3A:
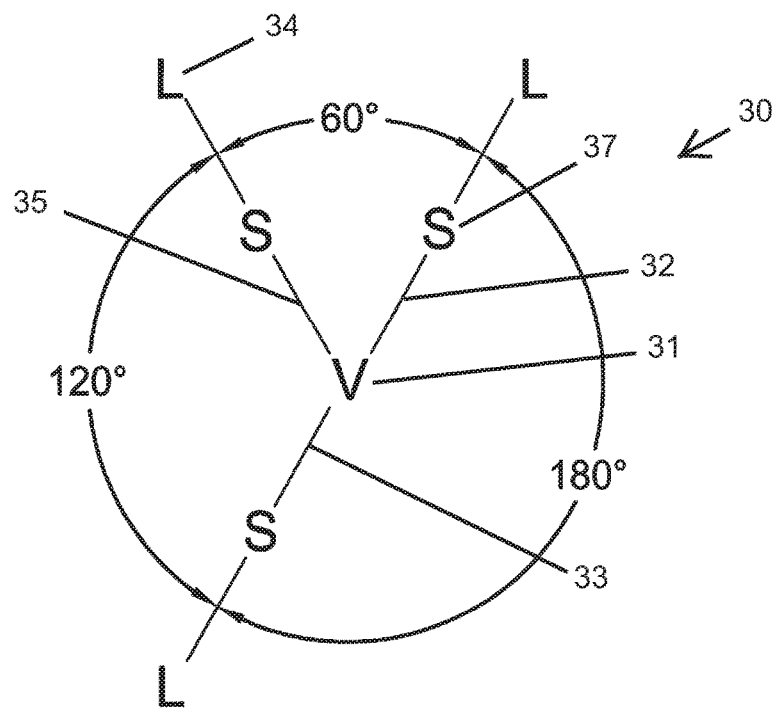
FIG. 3A is an exemplary schematic of a symmetrical Y-shaped monomer that may be employed to create metallotriangle-based nanomolecules in accordance with this invention.

With reference to FIG. 3A, an unsymmetrical Y-shaped monomer 30 includes a cyclic unsymmetrical Y-vertex group 31 with a first coordinating unsymmetrical Y-arm 32 and a second coordinating unsymmetrical Y-arm 33 extending from the cyclic unsymmetrical Y-vertex group 31 at 180° from one another, and a third coordinating unsymmetrical Y-arm 35 extending at 120° from the second coordinating unsymmetrical Y-arm 33 (and 60° from said first coordinating Y-arm), each of the first, second, and third coordinating unsymmetrical Y-arms 32, 33, 35 terminating in a metal-coordinating unsymmetrical Y-ligand 34. In some embodiments, the coordinating unsymmetrical Y-arms 32, 33, 35 include a spacer group 37 between the cyclic unsymmetrical Y-vertex group 31 and the metal coordinating ligands 34.

A specific exemplary unsymmetrical Y-shaped monomer is provided below:

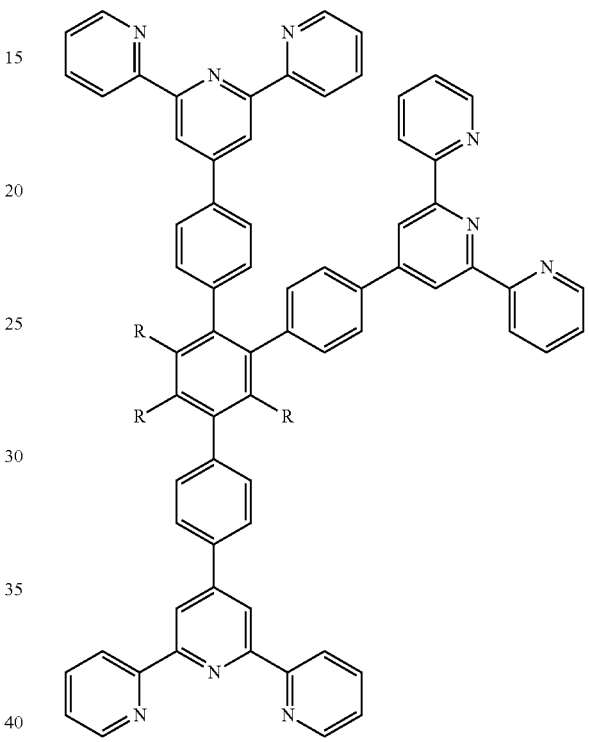

where the R's represent H, alkyl, aryl, alkoxyl, aryloxy, aralkyl, aralkyl-oxy, or any other similar substituent(s), including but not limited to heteroatoms (e.g., O, P, N, S) in said position. This monomer is best envisioned as trisubstitution from the 1,2,4-directivity of 1,2,4-benzene or an unsymmetrical trisubstitution pattern of which possess a precise unsymmetrical "Y" directionality. This is more akin to a lowercase "y" shape, whereas the next disclosed monomer is more akin to an uppercase "Y".

Figure 3B:
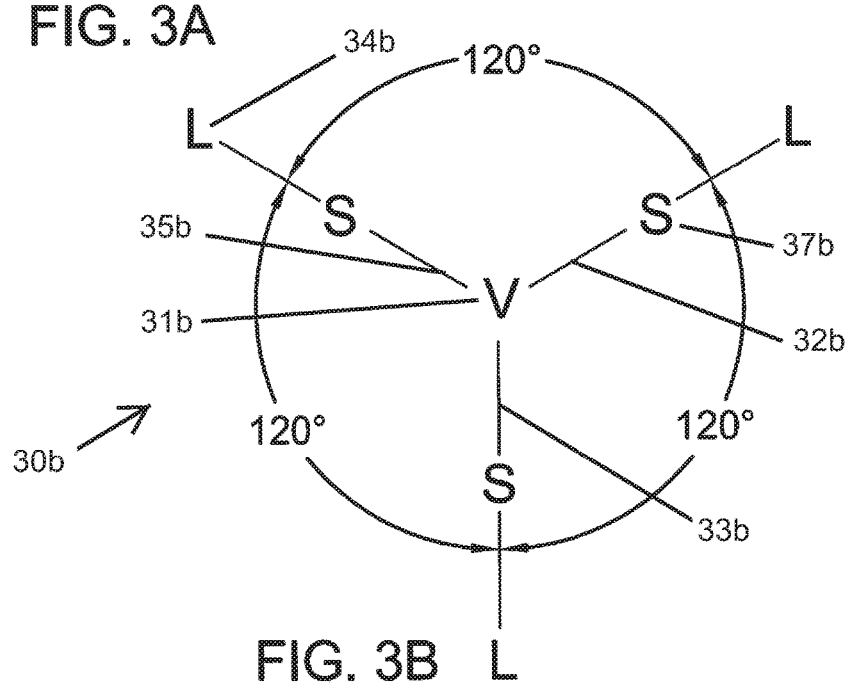
FIG. 3B is an exemplary schematic of an unsymmetrical Y-shaped monomer that may be employed to create metallotriangle-based nanomolecules in accordance with this invention.

With reference to FIG. 3B, a symmetric Y-shaped monomer 30b includes a cyclic symmetric Y-vertex group 31b with a first coordinating symmetric Y-arm 32b, second coordinating symmetric Y-arm 33c, and third coordinating symmetric Y-arm 35b, each extending from the cyclic symmetric Y-vertex group 31b at 120° intervals, and each of the first, second, and third coordinating symmetric Y-arms 32b, 33b, 35b terminating in a metal-coordinating symmetric Y-ligand 34b. In some embodiments, the coordinating symmetric Y-arms 32b, 33b, 35b include a spacer group 37b between the cyclic symmetric Y-vertex group 31b and the metal coordinating ligands 34b.

A specific exemplary symmetric Y-shaped monomer is provided below:

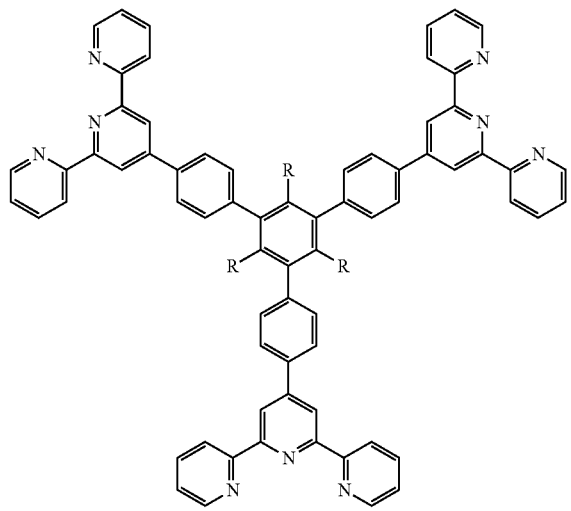

where the R's represent H, alkyl, aryl, alkoxyl, aryloxy, aralkyl, aralkyl-oxy, or any other similar substituent(s), including but not limited to heteroatoms (e.g., O, P, N, S) in said position. This monomer is best envisioned as trisubstitution from the 1,3,5-directivity of 1,3,5-benzene or trisubstitution of tris-meta substituted positions which possess a precise symmetrical "Y" directionality.

Figure 4:
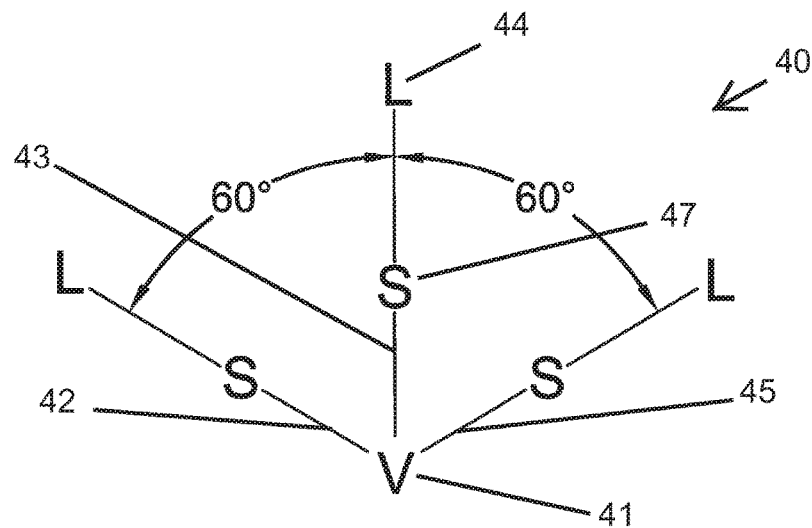
FIG. 4 is an exemplary schematic of a W-shaped monomer (or alternatively conceptualized as a double-V shape) that may be employed to create metallotriangle-based nanomolecules in accordance with this invention.

With reference to FIG. 4, a W-shaped monomer 40 includes a cyclic W-vertex group 41 with a first coordinating W-arm 42 and a second coordinating W-arm 43 extending from the cyclic W-vertex group 41 at 60° from one another, and a third coordinating W-arm 45 extending at 60° from the second coordinating W-arm 43 (and 120° from the first coordinating W-arm), each of the first, second, and third coordinating W-arms 42, 43, 45 terminating in a metal-coordinating unsymmetrical W-ligand 44. In some embodiments, the coordinating W-arms 42, 43, 45 include a spacer group 47 between the cyclic W-vertex group 41 and the metal coordinating ligands 44.

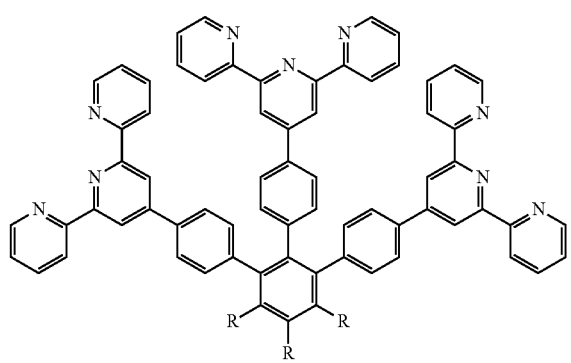

where the R's represent H, alkyl, aryl, alkoxyl, aryloxy, aralkyl, aralkyl-oxy, or any other similar substituent(s), including but not limited to heteroatoms (e.g., O, P, N, S) in said position. This monomer is best envisioned as trisubstitution from the 1,2,3-directivity of 1,2,3-trisubstituted benzene or an unsymmetrical trisubstitution pattern of which possess a precise unsymmetrical "W" directionality.

Figure 5:
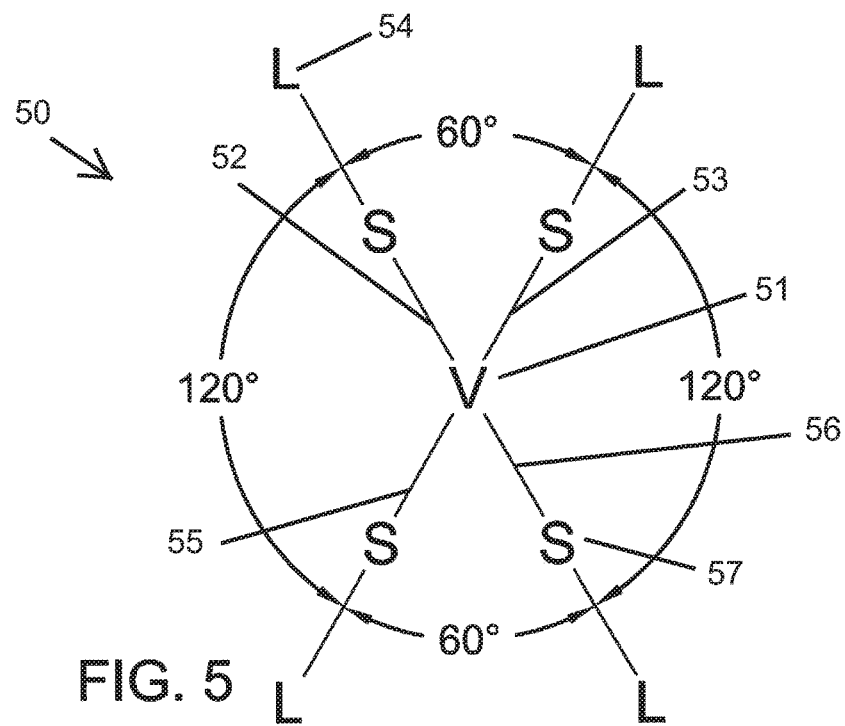
FIG. 5 is an exemplary schematic of a X-shaped monomer that may be employed to create metallotriangle-based nanomolecules in accordance with this invention.

With reference to FIG. 5, an X-shaped monomer 50 include a cyclic X-vertex group 51 with a first coordinating X-arm 52 and a second coordinating X-arm 53 extending from the cyclic X-vertex group 51 at 60° from one another, and opposed third coordinating X-arm 55 and fourth coordinating X-arm 56 extending from the cyclic X-vertex group 51 at 60° from one another in a direction opposite to the first and second coordinating X-arms 52, 53, each of the first, second, third, and fourth coordinating X-arms 52, 53, 55, 56, terminating in a metal-coordinating X-ligand 54. In some embodiments, the coordinating X-arms 52, 53, 55, 56 include a spacer group 57 between the cyclic X-vertex group 51 and the metal coordinating ligands 54.

A specific exemplary X-shaped monomer is provided below:

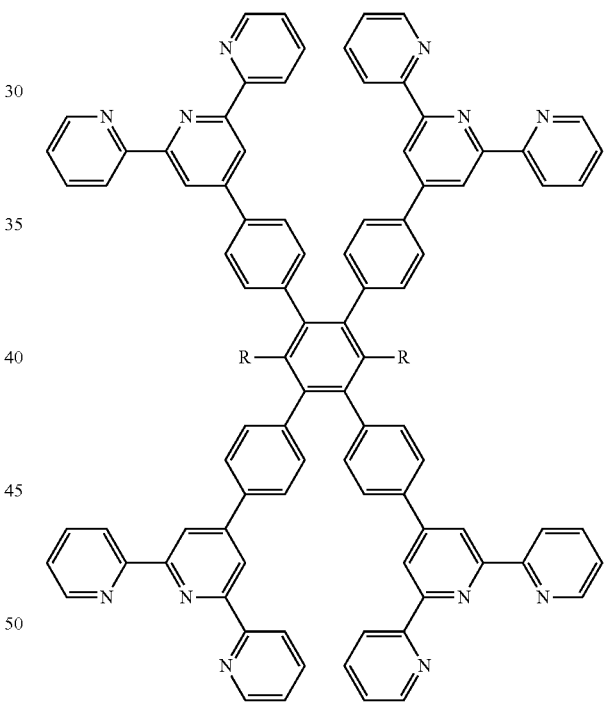

where the R's represent H, alkyl, aryl, alkoxyl, aryloxy, aralkyl, aralkyl-oxy, or any other similar substituent(s), including but not limited to heteroatoms (e.g., O, P, N, S) in said position. This monomer is best envisioned as tetrasubstitution from the 1,2,4,5-directivity of 1,2,4,5-benzene or an unsymmetrical tetrasubstitution pattern of which possess a precise unsymmetrical "X" directionality.

Figure 6:
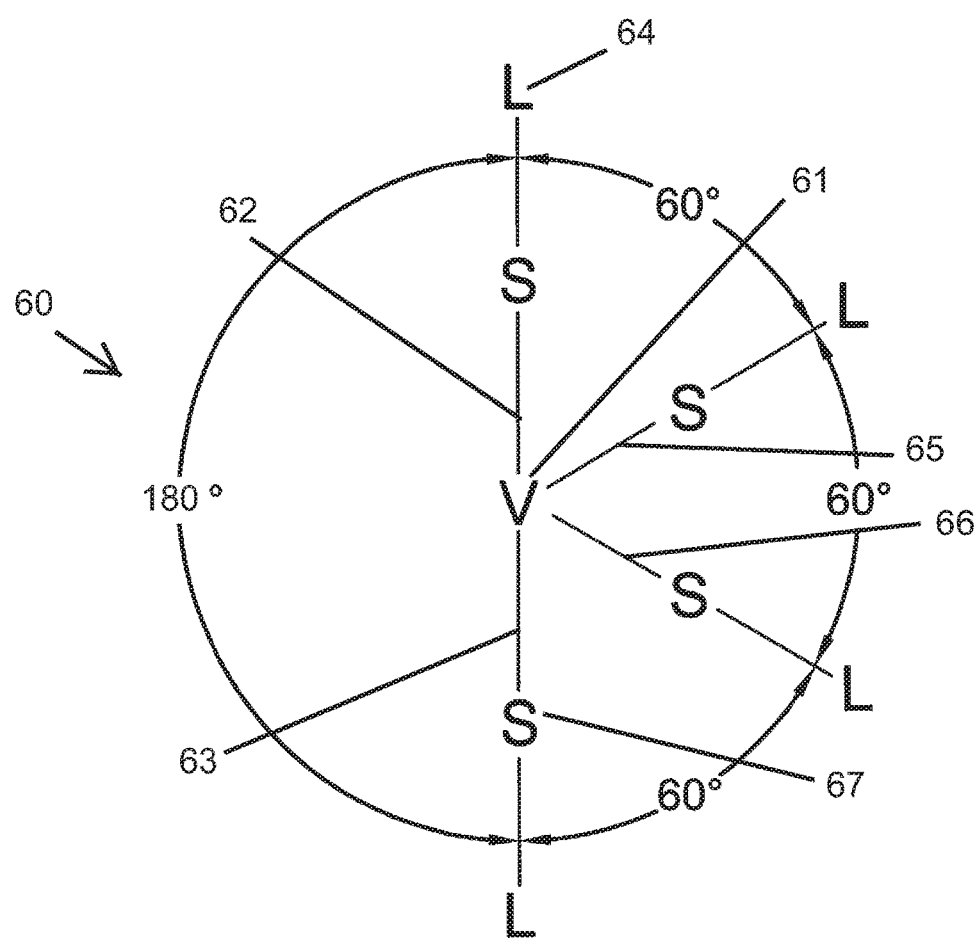
FIG. 6 is an exemplary schematic of a K-shaped monomer that may be employed to create metallotriangle-based nanomolecules in accordance with this invention.

With reference to FIG. 6, a K-shaped monomer 60 includes a cyclic K-vertex group 61 with a first coordinating K-arm 62 and a second coordinating K-arm 63 extending from the cyclic K-vertex group 61 at 180° from one another, a third coordinating K-arm 65 extending from the cyclic K-vertex group 61 at 60° from the first coordinating K-arm 62 and at 120° from the second coordinating K-arm 63, and a fourth coordinating K-arm 66 extending from the cyclic K-vertex group 61 at 60° from the second coordinating K-arm 63 and at 120° from the first coordinating K-arm 62, the third and fourth coordinating K-arms 65, 66 extending from the cyclic K-vertex group 61 at 60° from one another, each of the first, second, third, and fourth coordinating K-arms 62, 63, 65, 66 terminating in a metal-coordinating K-ligand 64. In some embodiments, the coordinating K-arms 62, 63, 65, 66 include a spacer group 67 between the cyclic K-vertex group 61 and the metal coordinating ligands 64.

A specific exemplary K-shaped monomer is provided below:

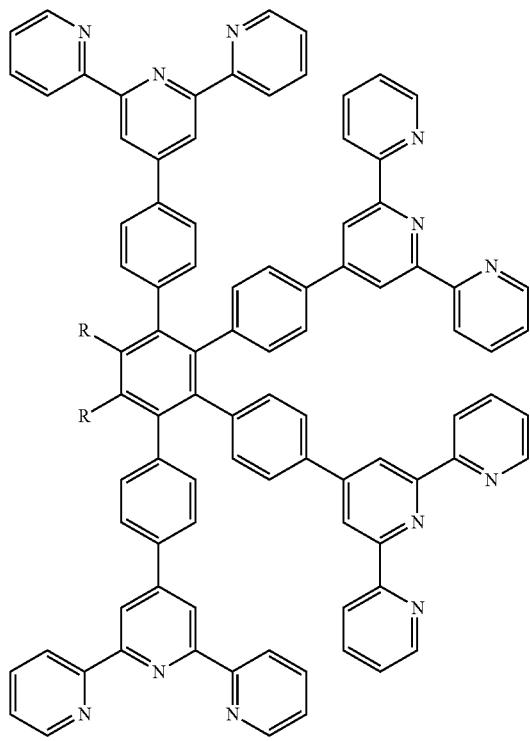

where the R's represent H, alkyl, aryl, alkoxyl, aryloxy, aralkyl, aralkyl-oxy, or any other similar substituent(s), including but not limited to heteroatoms (e.g., O, P, N, S) in said position. This monomer is best envisioned as tetrasubstitution from the 1,2,3,4-directivity of 1,2,3,4-benzene or an unsymmetrical tetrasubstitution pattern of which possess a precise unsymmetrical "K" directionality.

Figure 7:
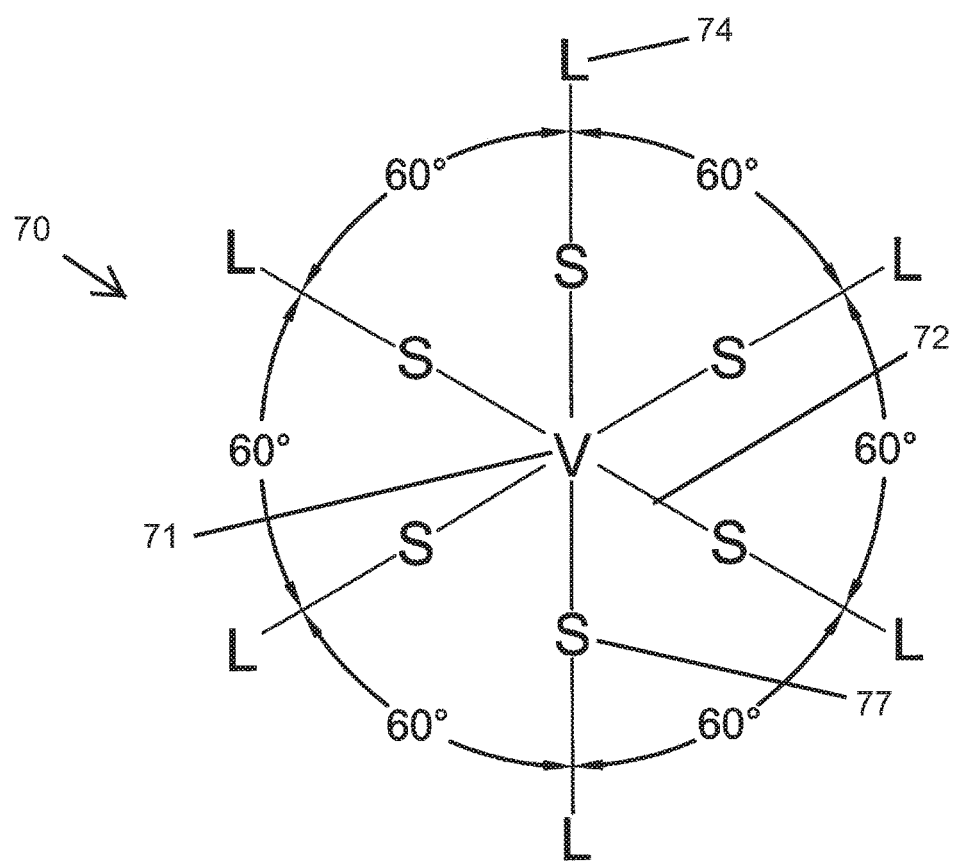
FIG. 7 is an exemplary schematic of a hex-star-shaped monomer that may be employed to create metallotriangle-based nanomolecules in accordance with this invention.

With reference to FIG. 7, a hex-star-shaped monomer 70 includes a cyclic hex-star-vertex group 71 having six coordinating hex-star-arms 72 extending from the cyclic hex-star-vertex group 71 at 60° intervals and each terminating in a metal-coordinating hex-star-ligand 74. In some embodiments, the coordinating star-arms 72 include a spacer group 77 between the cyclic hex-star-vertex group 71 and the metal coordinating ligands 74.

A specific exemplary hex-star-shaped monomer is provided below:

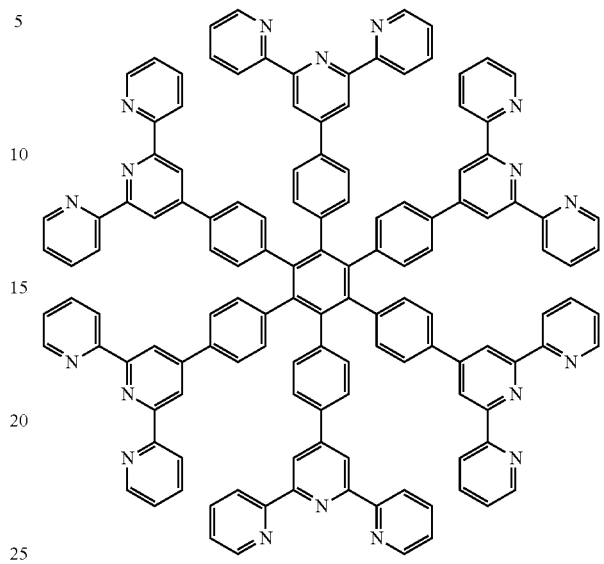

This monomer is best envisioned as hexasubstitution from the 1,2,3,4,5,6-directivity of 1,2,3,4,5,6-benzene or hexasubstitution pattern of which possess a precise hexa-directionality; this monomer is used as an internal branching component.

Figure 8:
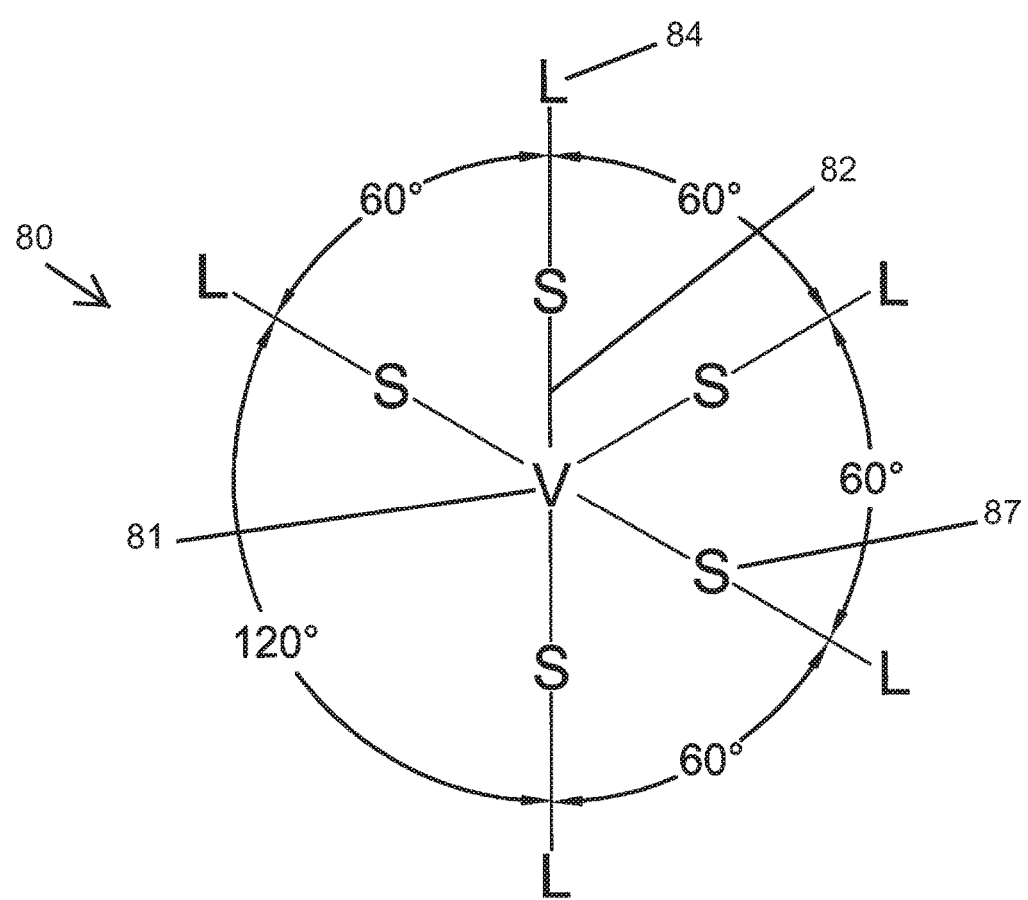
FIG. 8 is an exemplary schematic of a penta-star-shaped monomer that may be employed to create metallotriangle-based nanomolecules in accordance with this invention.

With reference to FIG. 8, a penta-star-shaped monomer 80 includes a cyclic penta-star-vertex group 81 having five coordinating penta-star-arms 82 extending from the cyclic penta-star-vertex group 81 at 60° intervals and each terminating in a metal-coordinating penta-star-ligand 84. There is a 120° gap between the first and last arm. In some embodiments, the coordinating star-arms 82 include a spacer group 87 between the cyclic penta-star-vertex group 81 and the metal coordinating ligands 84.

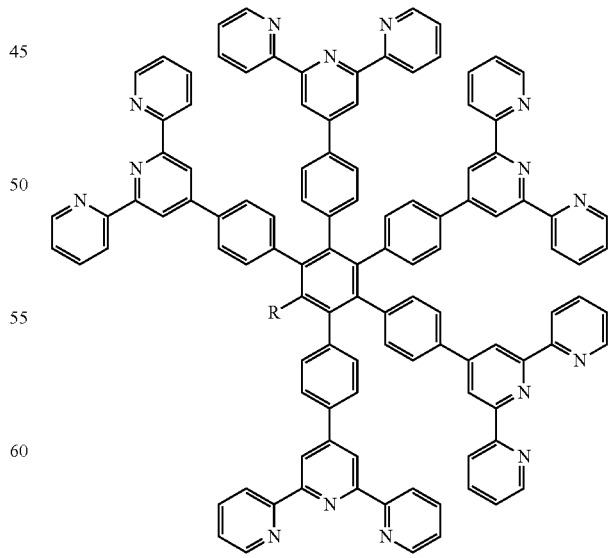

where the R's represent H, alkyl, aryl, alkoxyl, aryloxy, aralkyl, aralkyl-oxy, or any other similar substituent(s), including but not limited to heteroatoms (e.g., O, P, N, S) in said position. This monomer is best envisioned as pentasubstitution from the 1,2,3,4,5-directivity of 1,2,3,4,5-benzene or pentasubstitution pattern of which possess a precise penta-directionality.

It should be appreciated that the R group definitions provided above apply equally well to the more conceptual structures of FIGS. 1-8.

The above rigid core directional components can be expanded using the "I" monomeric components to expand the size of the overall structure. In particular embodiments, the termini of the arms can be selected from 4'-substituted terpyridine, 4-substituted pyridine, 4- or 5-substituted bipyridine 4-benenecarboxylate or carboxylate.

A plurality of specifically selected poly-ligand monomers are mixed with an appropriate plurality of metal ions. The number and type of poly-ligand monomers and the number of metal ions are chosen and mixed in stoichiometric ratios such that, after said step of mixing, the metallotriangle-based nanomolecule self-assembles through the coordination of all of the metal coordinating V-, wide V-, X-, symmetric Y-, unsymmetrical Y-, K-, W-, hex-star-, penta-star-, and I-ligands with the plurality of metal ions. In some embodiments, the cyclic V-, wide V-, X-, symmetric Y-, unsymmetrical Y-, K-, W-, hex-star-, penta-star-vertex groups each define at least one vertex of a triangle or triangle-based overall structure or substructure of the assembled nanomolecule. In some embodiments, all coordinating ligands coordinate with a metal ion. In some embodiments, the cyclic V-, wide V-, X-, symmetric Y-, unsymmetrical Y-, K-, W-, hex-star-, penta-star-vertex groups each define at least one vertex of a triangle or triangle-based overall structure or substructure of the assembled nanomolecule. In some embodiments, all metal ions are involved in a coordination with coordinating ligands. In some embodiments, all coordinating ligands coordinate with a metal ion, all metal ions are involved in a coordination with coordinating ligands, and the cyclic V-, wide V-, X-, symmetric Y-, unsymmetrical Y-, K-, W-, hex-star-, penta-star-vertex groups each define at least one vertex of a triangle or triangle-based overall structure or substructure of the assembled nanomolecule.

In some embodiments, the metal coordinating V-, wide V-, X-, symmetric Y-, unsymmetrical Y-, K-, W-, hex-star-, penta-star-, and I-ligands are selected from the group consisting of monodentate ligands, bidentate ligands, and tridentate ligands. In some embodiments, at least two of the metal coordinating V-, wide V-, X-, symmetric Y-, unsymmetrical Y-, K-, W-, hex-star-, penta-star-, and I-ligands are tridentate ligands and at least two of those tridentate ligands coordinate with a given metal ion. In some embodiments, each of the metal coordinating V-, wide V-, X-, symmetric Y-, unsymmetrical Y-, K-, W-, hex-star-, penta-star-, and I-ligands is a tridentate ligand. For improved structural integrity, in some embodiments, the tridentate ligands coordinate with one of the plurality of metal ions to bind 6 atoms thereto.

In some embodiments, the metal coordinating V-, wide V-, X-, symmetric Y-, unsymmetrical Y-, K-, W-, hex-star-, penta-star-, and I-ligands are selected from pyridines, bipyridines, terpyridines, pyrroles, polypyrroles thiophenes, polythiophenes, phosphines, polyphosphines, isoxazoles, oxazoles, pyrimidines, polypyrimidines, pyridazines, poly pyridazines, polyoxazoles, thiazoles, and polythiazoles. In some embodiments, the metal coordinating V-, wide V-, X-, symmetric Y-, unsymmetrical Y-, K-, W-, hex-star-, penta-star-, and I-ligands are selected from, but not limited to, terpyridines, terthiophenes, polypyrroles, pyridinopyrrole, pyridinothiophene, polyarylpyridino, and polypyrrolopyridine.

In some embodiments, the cyclic V-, wide V-, X-, symmetric Y-, unsymmetrical Y-, K-, W-, hex-star-, penta-star-, and I-vertex groups are selected from aromatic rings with 5 or more atoms in the ring structure. Vertex groups are chosen with regard to the desired component restrictions, such as shape-persistence, juxtaposition of substituents and symmetry. A vertex is not limited to simple aryl units but vertex characteristics can be realized in more complex structures, such as for example, coronenes, cholesterols, and porphyrins, to mention but a few. In some embodiments, the cyclic V-, wide V-, X-, symmetric Y-, unsymmetrical Y-, K-, W-, hex-star-, penta-star-, and I-vertex groups are selected from aromatic rings with 6 atoms in the ring structure. It will be appreciated that for metallotriangular-based nanomolecule self-assembly, the 6 atom ring provides suitable binding sites for the coordinating arms to extend at the desired angles for formation of the desired shaped poly-ligand monomers.

In some embodiments, the cyclic V-, wide V-, X-, symmetric Y-, unsymmetrical Y-, K-, W-, hex-star-, penta-star-, and I-vertex groups are selected from phenyl groups, polyarylenes and heteroaromatic, polyheteroaromatic, rigid cycloalkanes and cholesteric. In some embodiments, the cyclic V-, wide V-, X-, symmetric Y-, unsymmetrical Y-, K-, W-, hex-star-, penta-star-, and I-vertex groups are all phenyl groups.

In some embodiments, spacer groups are selected from any 1, 2 or 3 cyclic groups bound in a row at 180 degrees, making a straight arm. In some embodiments, spacer groups are selected from phenyl, biphenyl, p-terphenyl, polyarylenes and heteroaromatic, polyheteroaromatic, rigid cycloalkanes, cholesteric and alkyne, aralkyne, diazo and polydiazo groups. In some embodiments, spacer groups are selected from phenyl, biphenyl, p-terphenyl. In some embodiments, the spacer groups are all selected so that the coordinating arms of all poly-ligand monomers are the same length. In some embodiments, all spacer groups are phenyl groups.

The self-assembly takes place in an appropriate solvent, with the plurality of poly-ligand monomers and plurality of metal ions introduced into the solvent and allowed to self-assemble. In some embodiments, the solvent is selected from organic solvents. In some embodiments the solvent is selected from alcohols, aromatics, alkanes, alkenes, halocarbons, polar protic, polar aprotic and nonpolar liquids. In some embodiments, the solvent is selected from MeOH and CHCl3, $CH_2Cl_2$, toluene, benzene, and ethylene glycol.

The metal ions are chosen from any metal ions suitable for coordinating with the particular metal coordinating ligands employed. In some embodiments, the metal ions employed have an oxidation state of +2. In some embodiments, the metal ions are selected from the group consisting of $Fe^{+2}$, $Ru^{+2}$, $Os^{+2}$, $Ir^{+2}$, $Zn^{+2}$, $Cn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof. In some embodiments, the metal ions are selected from the group consisting of $Zn^{+2}$, $Cn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$ and combinations thereof. In some embodiments, the metal ions are selected from the group consisting of $Fe^{+2}$, $Ru^{+2}$, $Os^{+2}$, $Ir^{+2}$, $Zn^{+2}$, $Cd^{+2}$ and combinations thereof. In some embodiments, the metal ions are selected from 55 known metals that have been reported to complex in such terpyridine systems; simple and branched pyridines as well as carboxylates are known to complex with most metals in the periodic chart.

In some embodiments, the metal ions are added to the solvent in the form of a pure metal salt or in some cases as a hydrate compounds. It is critical that the proper stiochiometric ratios of ligand(s) to metal centers be quantitatively ascertained to ensure that there are no "open ends". These metalloconstructs can also be used reagents for the construction of larger nanomolecular construction. This helps to ensure that the stoichiometry is more accurate, since the use of hydrated metals can be misleading due to the uncertain degree of hydrate.

In some embodiments, the ligands are terpyridine ligands and the metal is selected from any metal known to coordinate with terpyridine.

In some embodiment, the metal ions in the metallotriangle-based nanomolecule are all the same.

In some embodiments, the metallotriangle-based nanomolecule is employed as a nano-antenna, and the metal ions are selected from Zn, Cd, Fe, Ru, and Os.

In some embodiments, the metallotriangle-based nanomolecule is employed as a molecular host framework for molecular guests, and the metal ions are selected from Zn, Cd, Fe, Ru, and Os.

In some embodiments, counter ions are also included in the solvent to form a metal ion-counter ion pair that is soluble in the solvent. In some embodiments, the metal ions have a counter ion selected from $Br^-$, $I^-$, $ClO_4^-$, $PF_6^-$, $PF_4^-$, carboxylic acids, polycarboxylic acids, triflate, bis[2,2':6', 2"terpyridine-$(CO_2^-)_n$, and dendrimers with surface.

Figure 9:
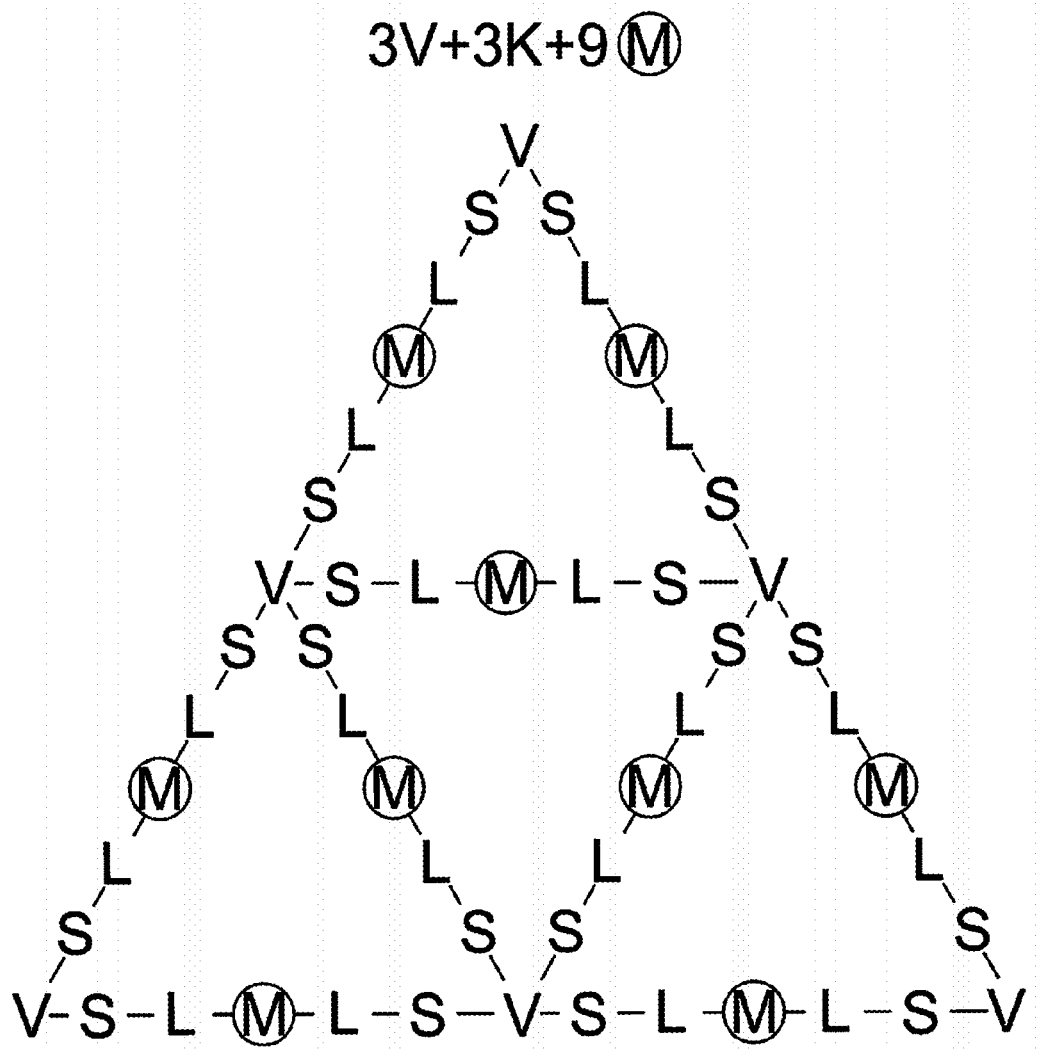
FIG. 9 is a general schematic of a construct mimicking a first-generation Sierpinski triangle, formed of 3 V-shaped monomers, 3 K-shaped monomers, and 9 metal ions.
Figure 10:
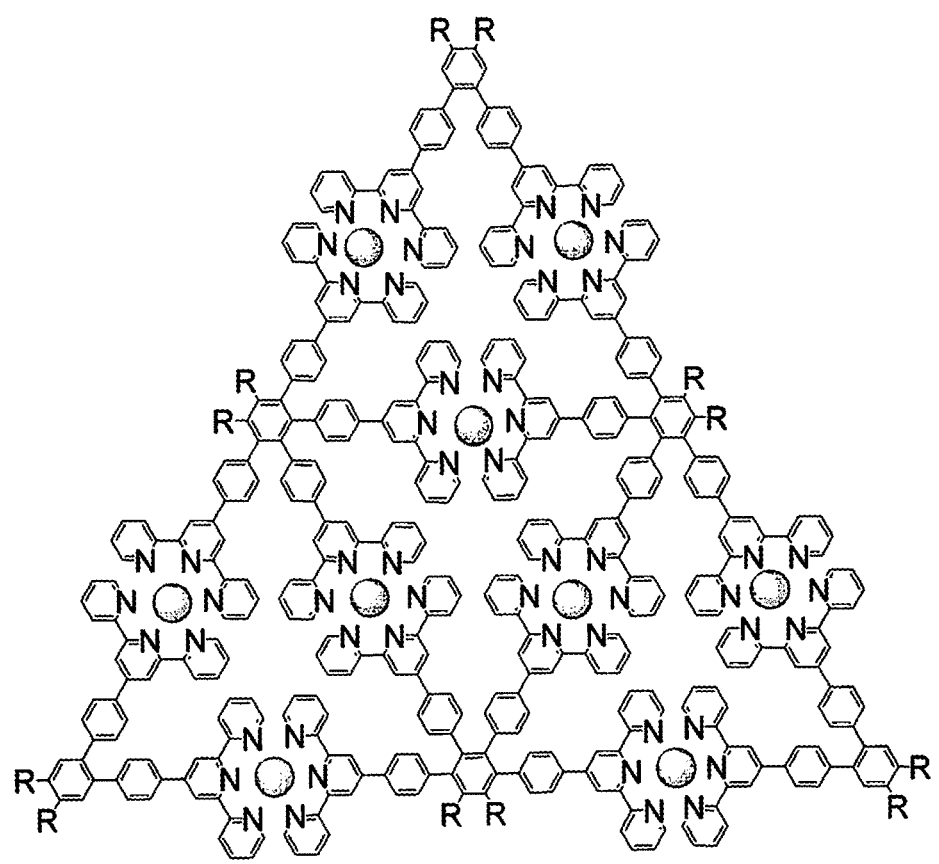
FIG. 10 is a specific embodiment of the general schematic of FIG. 9.

The general method is already evident from the disclosures above. Appropriately selected poly-ligand monomers are mixed in appropriate ratios with an appropriate number of metal ions, and the coordinating ligands of the poly-ligand monomers coordinate with the metals to form the metallotriangle-based nanomolecule. The method will typically begin with a selection of a desired metallotriangle-based nanomolecular structure. As will be apparent from the general disclosures and examples below, the desired nanomolecular structure can be mapped out or otherwise envisioned pre-assembly by the one designing the nanomolecular. For example, with reference to the general nanomolecule structure of FIG. 9—and the related specific nanomolecule of FIG. 10 as specifically disclosed in Example 1 herein below—a triangle-shaped nanomolecular in accordance with this invention can be created by mixing 3 V-shaped monomers, 3 K-shaped monomers, and 9 metal ions. As seen in FIGS. 9 and 10 the choice of shaped monomers and stoichiometric ratios between those monomers and the metal ions dictates the end shape of the nanomolecule. Thus, in accordance with the teaching provided herein, the number and type of metallotriangle-based nanomolecules that can be formed is virtually endless. Indeed, through the use of the various shaped monomers in precise ratios with metal ions, new architectures are limited only by one's imagination. Additional examples will help to elucidate this point.

Figure 11:
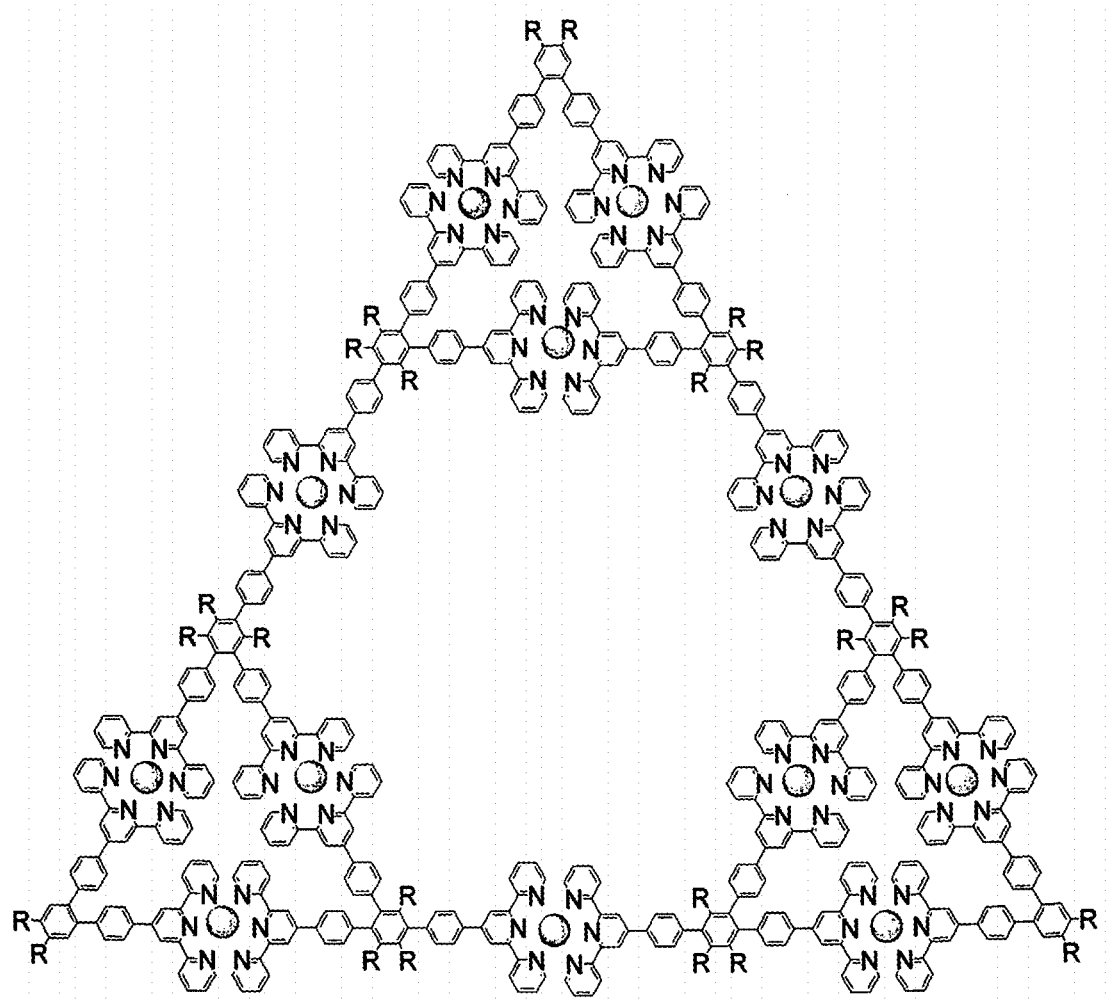
FIG. 11 is a general schematic of a different metallotriangle-based nanomolecule having a more hollow interior in light of the choice of Y-shaped monomers, the nanomolecule being formed from 3 V-shaped monomers, 6 Y-shaped monomers, and 12 metal ions.

With reference to FIG. 11, it can be seen that a slightly larger and centrally hollow metallotriangle-based nanomolecule can be formed from the mixing of 3 V-shaped monomers, 6 Y-shaped monomers, and 12 metal ions.

Figure 12:
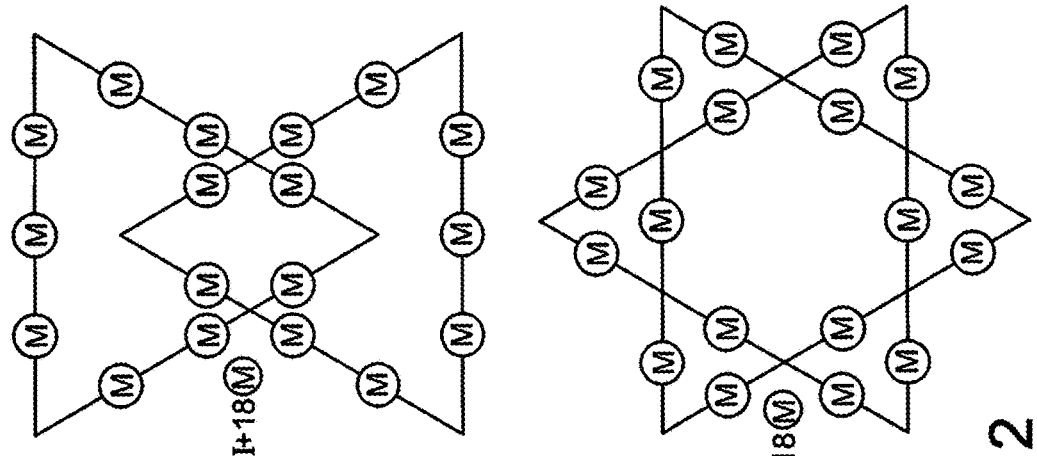
FIG. 12 schematically represents 4 different nanomolecule structures in accordance with this invention, the structure being formed by conceptually changing the position of two triangular motifs.
Figure 12:
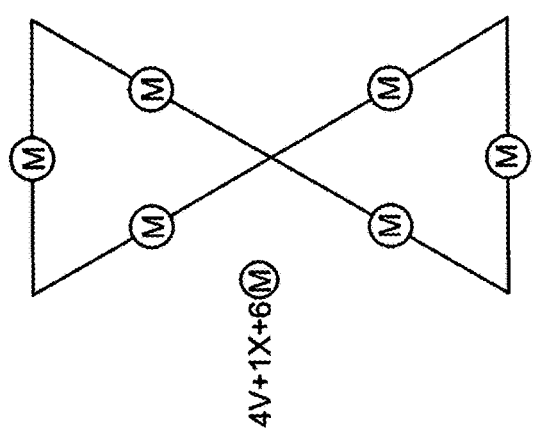
Figure 12:
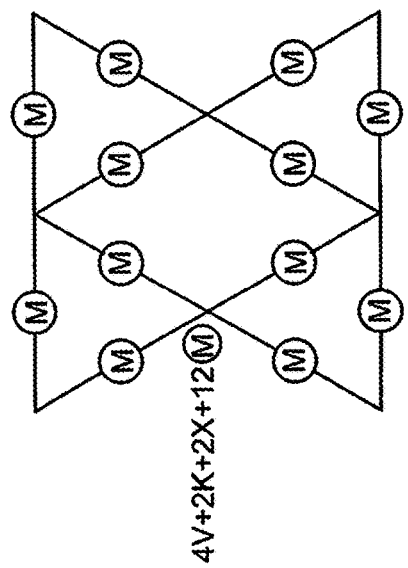

Consideration of two triangular motifs can lead to several accessible shapes simply by changing the position of those triangles, as seen in FIG. 12. In the structure on the left, two triangles are placed atop one another, and this bowtie structure can be formed by the mixing of 4 V-shaped monomers, 1 X-shaped monomer, and 6 metal ions. Proceeding to mentally overlap the two triangles produces the second structure (from the left), which provides an interior rhombus shape, and is formed of 6 V-shaped monomers, 8 I-shaped monomers, and 2 X-shaped monomers coordinating with 18 metal ions. Further continued progression of the triangles toward one another results in the polytriangle structure (third from the left), which is formed of 4 V-shaped monomers, 2 K-shaped monomers, and 2 X-shaped monomers coordinating with 12 metal ions. The last example of FIG. 12 shows a Star of David shape formed of 6 V-shaped monomers and 6 X-shaped monomers coordinating with 18 metal ions.

Figure 13:
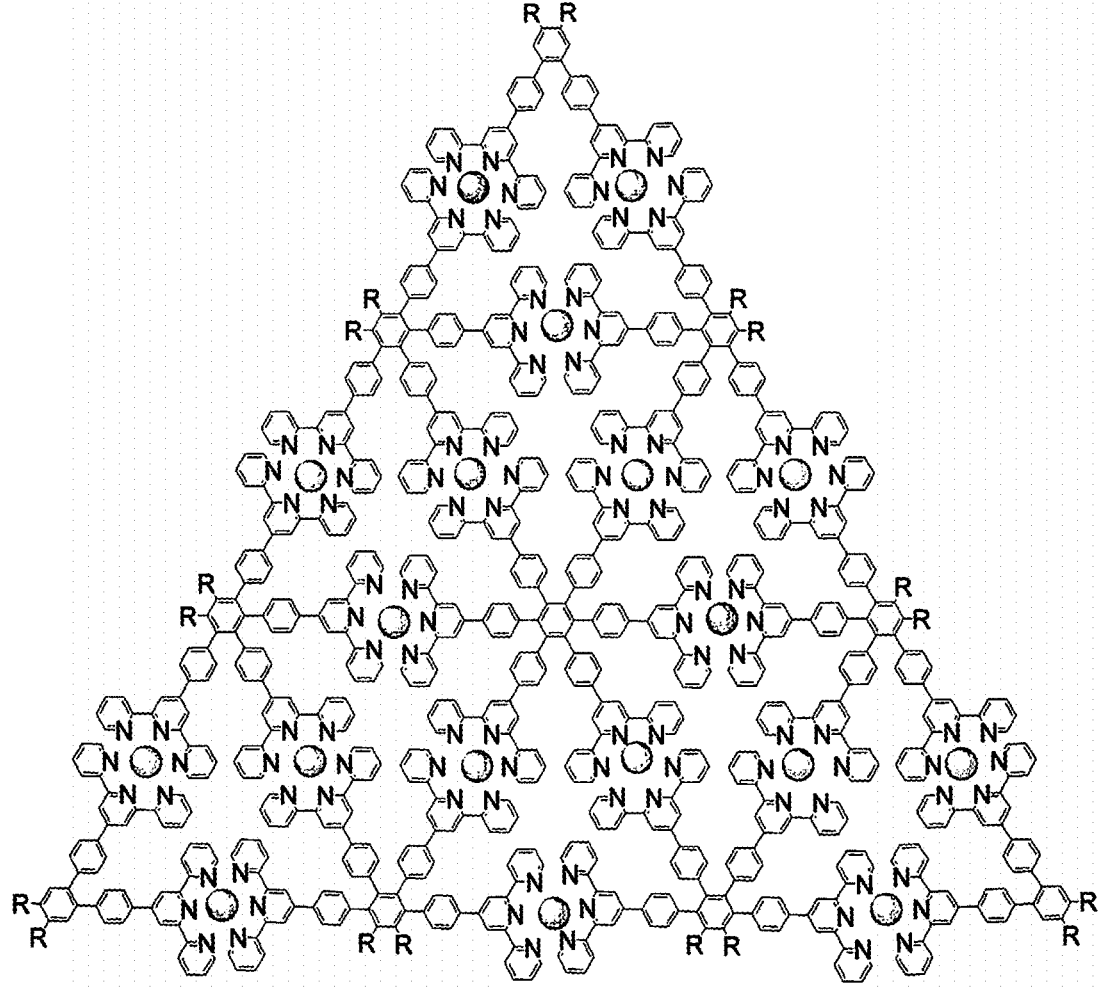
FIG. 13 is a general schematic of yet another metallotriangle-based nanomolecule, this one having a filled-in interior in light of use of a star-shaped monomer, and is formed of 3 V-shaped monomers, 6 K-shaped monomers, and 1 star-shaped monomer, all coordinated with 18 metal ions.

As seen in FIG. 13 shows how a star-shaped monomer might be employed. Notably, it serves to fill in an interior region of a larger triangular concept. The specific concept of FIG. 13 has 3 V-shaped monomers, 6 K-shaped monomers, and 1 star-shaped monomer, all coordinated with 18 metal ions. To further elucidate the point that structures are only limited by one's imagination, it is noted that the triangular structure of FIG. 13 could be made larger by combining 3 V-shaped monomers, 9 K-shaped monomers, 3 star-shaped monomers with 30 metal ions. The 3 star-shaped monomers would coordinate in the center (the 2 K-shaped monomers at the bottom of the structure of FIG. 13 would be replaced with star-shaped monomers, with the additional K-shaped monomers coordinating there around, adding a bottom row to the smaller triangle of FIG. 13).

Figure 14:
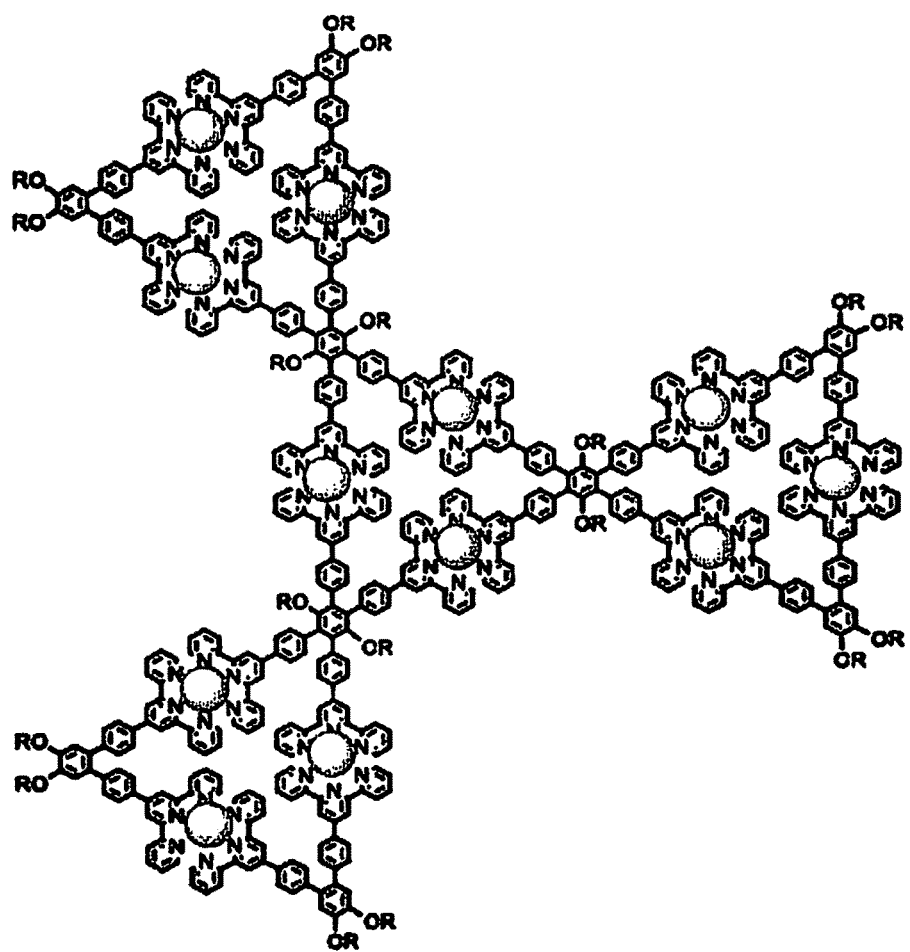
FIG. 14 is a general schematic of yet another metallotriangle-based nanomolecule, this one having a spoked triangle shaped, wherein identical triangular substructures extend from each vertex of an identical central triangle, and is formed of 6 V-shaped monomers and 3 X-shaped monomers coordinating with 12 metal ions.
Figure 15:
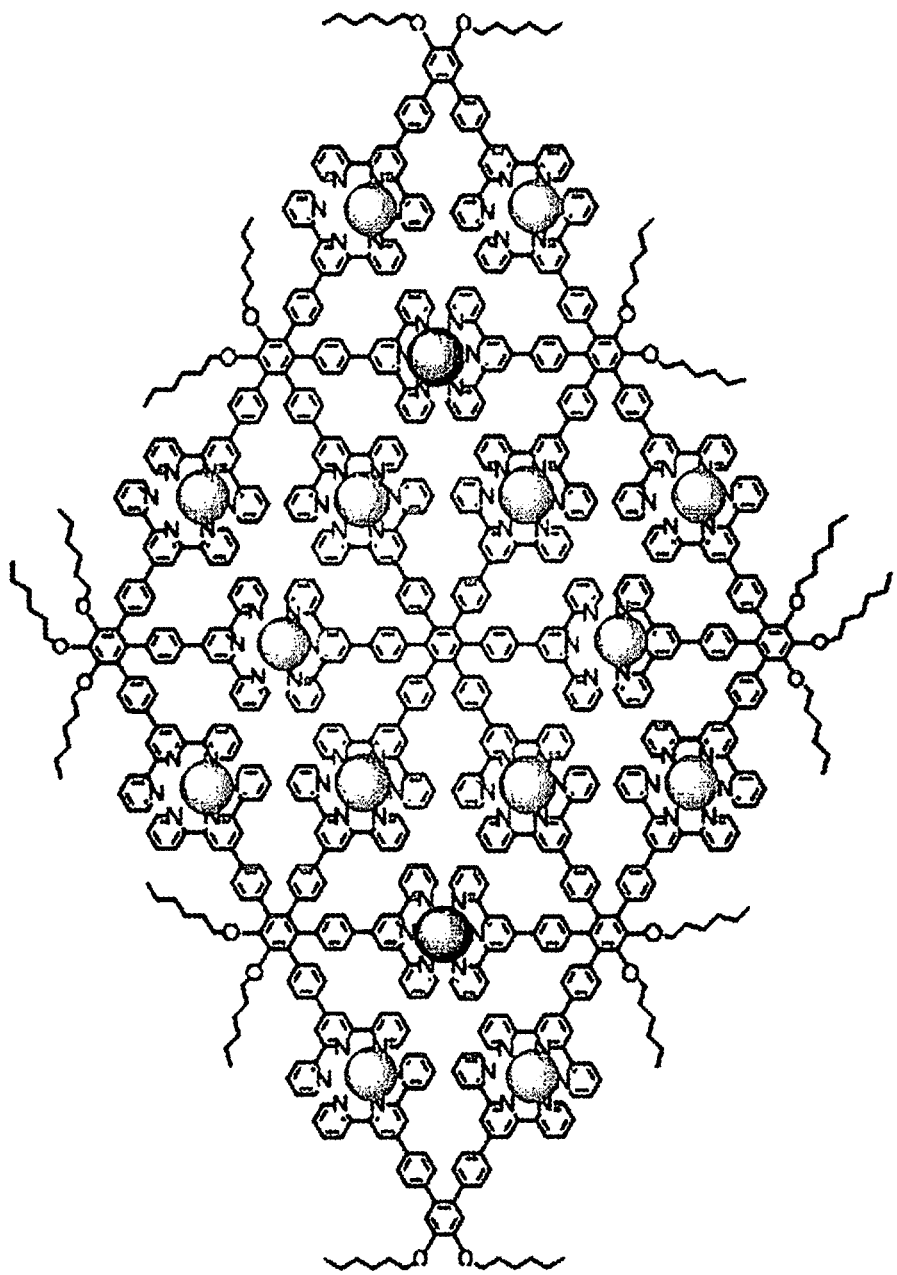
FIG. 15 is a general schematic of typical metallotriangle-based nanomacromolecule, this one having a diamond structure is formed by employing 2 V-shaped monomers, 4 K-shaped monomers, 1 star-shaped monomer, and 2 W-shaped monomers with 16 metal ions.

Additional complex shapes are shown in FIGS. 14 and 15.

FIG. 14 shows a spoked triangle shaped, wherein identical triangular substructures extend from each vertex of an identical central triangle, and is formed of 6 V-shaped monomers and 3 X-shaped monomers coordinating with 12 metal ions.

In FIG. 15, a diamond structure is formed by employing 2 V-shaped monomers, 4 K-shaped monomers, 1 star-shaped monomer, and 2 W-shaped monomers with 16 metal ions. FIG. 15 also shows that in some embodiments, the poly-ligand monomers can be selected to have additional alkyl chains (C1-C22) or PEG units to increase the solubility of the resultant complex(es). Increased hydrophobic and hydrophilic character of these large nanoconstructs is critical component for the resultant structural perfection.

EXAMPLES

Example 1—First Generation Sierpiński Triangle

Retro-synthetic analysis of a Sierpiński triangle revealed that it would require two easily accessible components for its assembly: a tetrakisterpyridine "K" monomer for the walls and core region and a ditopic 60°-directed "V" monomer for the vertices. Cadmium was chosen as the metal ion due to its thermodynamic lability. A 1:1 ratio of these "K" and "V" monomers was coupled with precisely 3 equivalents of $Cd^{II}$; the overall stability of the highly symmetric polytriangular architecture was projected to be favored over any oligomeric possibilities. In essence, there would be no loose ends or uncoordinated ligands. This is the most energetically desirable structure given the choice per QS of K and V monomers.

Figure 16:
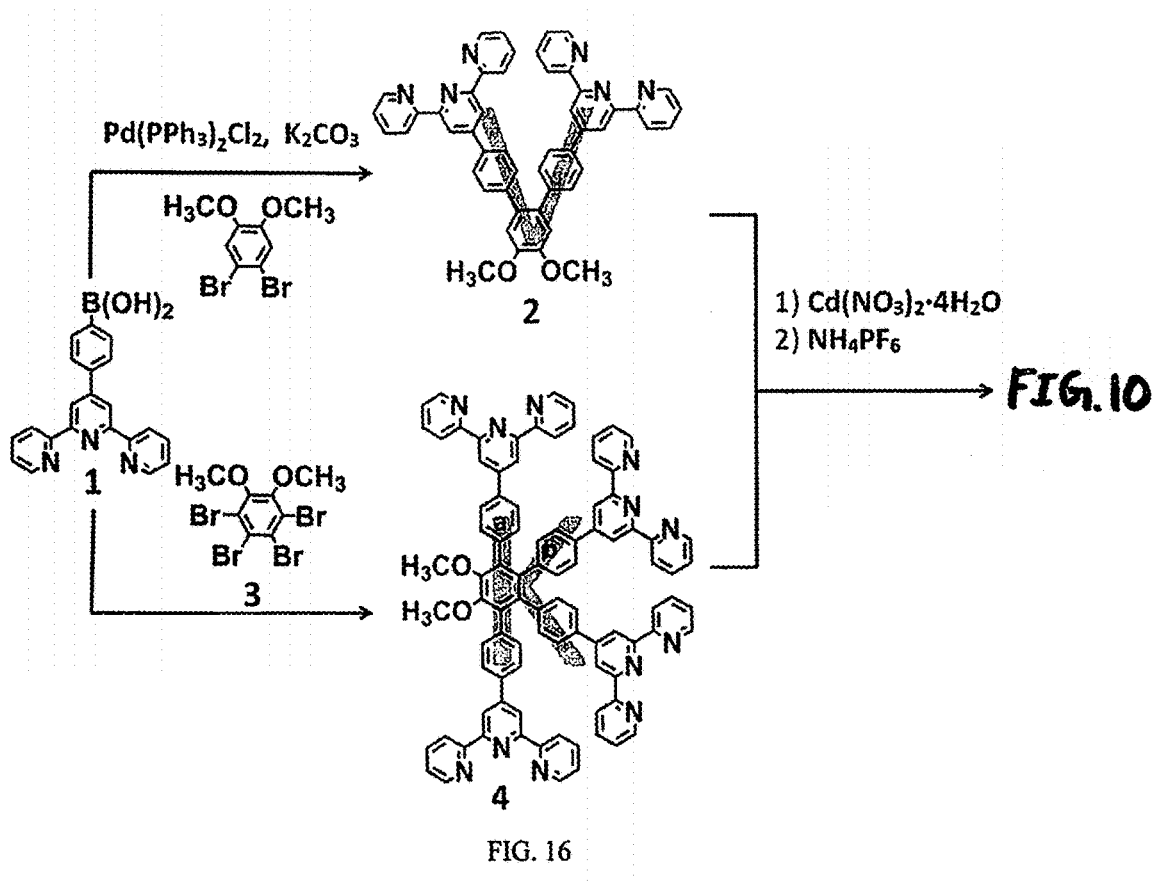
FIG. 16 shows a specific reaction scheme for the creation of V- and K-shaped monomers and their formation of the structure of FIG. 10.

Initially, a THF solution of 2,3,5,6-tetrabromocatechol and iodomethane (FIG. 16) was refluxed in an inert atmosphere ($N_2$, $K_2CO_3$, 12 h) generating 3. Boronic acid 1[31] was prepared using commercially available 4-formylphenylboronic acid. The desired "K" ligand 4 was easily synthesized (72%) from 3 by treatment with 1 using the standard Suzuki cross-coupling reaction, [$K_2CO_3$, $Pd(PPh_3)_2Cl_2$] under an atmosphere of Argon, [A. Schultz, X. Li, B. Barkakaty, C. N. Moorefield, C. Wesdemiotis, G. R. Newkome, J. Am. Chem. Soc. 2012, 134, 7672-7675]. Its $^1H$ NMR spectrum showed the characteristic peak at 3.76 ppm for the instilled OMe marker and the presence of two completely different arms (a and b). $^{13}$C NMR showed a peak at 60.76 ppm for the OMe.

All proton peaks were assigned using COSY and NOESY NMR spectroscopy. The $^{13}$C NMR assignments and MS data were in full agreement with the ligand structures. The colorless "V" ligand 2 was also synthesized (80%) by a slightly modified procedure from commercially available 4,5-dibromo-1,2-dimethoxybenzene under Suzuki cross-coupling conditions, according to previously cited Shultz, et al. It was easily characterized by $^1$H NMR spectroscopy and mass spectrometry. The aromatic region of ligand 2 showed one set of characteristic terpyridine peaks, one set of aromatic phenyl-spacer peaks and sharp singlet at 4.02 ppm for the OCH$_3$ markers. As well, the $^{13}$C NMR displayed a peak at 56.40 ppm for the OCH3 group.

The facile one-step assembly of the Sierpiński triangle 5 (FIG. 16) utilized an exact 1:1 solution of 2 and 4 in CHCl$_3$ to which a methanolic solution of 3 equivalents of Cd (NO$_3$)$_2$.4H$_2$O was added. The solution was stirred for 30 minutes at 25° C., then excess NH$_4$PF$_6$ was added to effect counterion exchange to PF$_6$. The desired PF$_6$ complex precipitated and was filtered and repeatedly washed with MeOH to remove excess NH$_4$PF$_6$. Complex 5 was obtained without any further purification as a light yellow solid in >95% yield.

The Sierpiński triangle 5 was completely characterized by $^1$H NMR, COSY, NOESY, ESI- and TWIM-MS, along with TEM. The $^1$H NMR spectrum of 5 showed the characteristics of <tpy-Cd$^{II}$-tpy> complex with a sharp and simple pattern indicative of a discrete structure with a high degree of inherent structural symmetry. The structural simplicity and symmetry were reflected in the $^1$H NMR spectrum. The imbedded methoxy markers within each ligand appear in the product as two distinct singlets at 3.98 (from "V") and 3.87 (from "K") ppm with a precise 1:1 ratio initially supporting a product that possesses D$_{3h}$ symmetry. Notably, there was an absence of peaks expected for polymeric structures and impurities. The aromatic region exhibited the expected ratio of peaks from three different sets of 3',5'-tpy protons for arms a, b, and c (8.92, 8.91 and 8.74 ppm. respectively; FIGS. 2 and 3); the downfield shifts result from deshielding upon complexation. The 6,6"-tpy protons are noticeably shifted upfield (7.92, 7.68 and 7.80 ppm, respectively, for a, b and c) when compared with the free ligands, as expected. All the peaks in the $^1$H NMR spectrum were assigned and verified with the aid of 2D-COSY and 2D-NOESY experiments and are in complete agreement with the proposed structure.

The $^{13}$C NMR spectrum of complex 5 exhibits three signals for the differing and readily identifiable 3',5'-tpy carbons at 158.39, 155.32, and 154.93 ppm, respectively, along with two, albeit very close, yet distinct peaks for the —OCH$_3$ substituents at 56.02 and 56.00 ppm, that further supports the proposed structure.

Sierpiński triangle 5 (metallotriangle-based nanomolecule) was further characterized by ESI-MS coupled with travelling-wave ion mobility (TWIM) mass spectrometry. Upon ESI-MS, a series of dominant peaks were generated at m/z 763.4, 854.2, 965.2, 1103.9, 1282.4, and 1520.3 corresponding to charge states from 11+ to 6+ from the loss of varying number of PF$_6$ anions. The isotope pattern of each peak is in agreement with the corresponding simulated isotope pattern. Additional evidence of the Sierpiński triangle 5 was provided by ESI-TWIM MS (FIG. 4) showing a set of single and narrow bands for charge states 11+ to 6+, in agreement with the presence of one single structure 5.

The structure of complex 5 was further confirmed by comparison of the experimental CCSs (collision cross-sections of charge states 11+ to 6+, deduced from their drift times measured by EST-TWIM MS, with theoretical CCS of the complex without any counterions (100 energy-minimized structures obtained by molecular modeling). Experimental and theoretical CCSs of triangle 5 are listed in Table 1-theoretical CCS was 1388.3 ((Å2); averaged).

TABLE 1

Drift times and collision cross-sections for the Sierpiński triangle 5.

| Charges | Drift time(ms) | CCS$_{exp}$(Å$^2$) |
|---|---|---|
| 6+ | 8.93 | 1309.2 |
| 7+ | 6.49 | 1295.5 |
| 8+ | 5.01 | 1288.7 |
| 9+ | 4.11 | 1297.2 |
| 10+ | 3.40 | 1288.5 |
| 11+ | 2.76 | 1242.3 |

Figure 17:
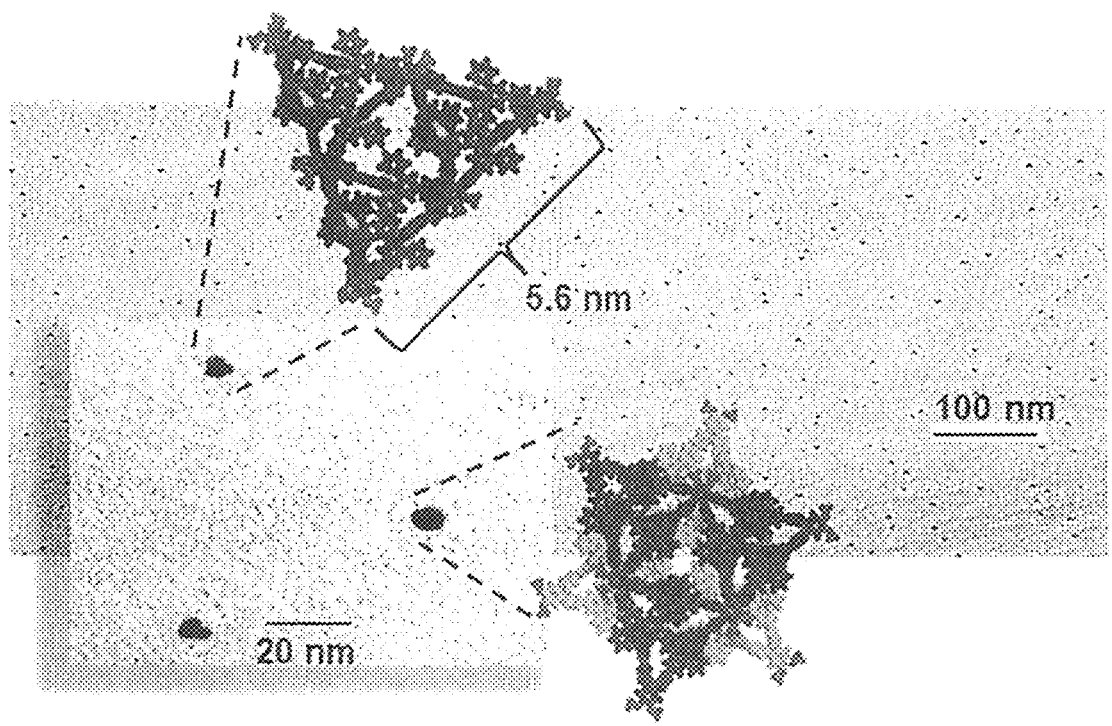
FIG. 17 is a low magnification, transmission electron microscope (TEM) image of the structure of FIG. 10 (Sierpiński triangle) showing a uniform field of particles, wherein the image clearly exhibits triangular motifs and a slightly larger and rounded picture of a proposed aggregate, analogous to the Star of David.

Transmission electron microscopy (TEM) afforded visualization of the triangle 5 which revealed direct correlation of both size and shape of single molecules upon deposition of a dilute (~10$^{-5}$ M) MeCN solution of complex 5 with PF$_6^-$ counterions on carbon-coated copper grids (300 mesh). The molecular framework is observed as a uniform dispersion of individual molecules with triangular shape, clear edges and discernable vertices. The average distance (5.6 nm) between the vertices correlates well with the size obtained from the optimized molecular model (FIG. 17).

The TEM image (FIG. 17) also suggests stacking or aggregation at higher concentration, where two Sierpiński triangles lie atop each other to generate a "Star of David"-like motif. This phenomenon is supported by $^1$H NMR experiments, where at higher concentrations a small extra peak is observed on the shoulder of the peak assigned to the ligand "K" —OCH$_3$ markers; thus, the NMR spectrum is a combination of stacked and individual species. At lower concentrations, a single peak for these markers is observed. The "V" ligand marker signals are unaffected by the concentration.

In conclusion, we have achieved the self-assembly of a first-generation Sierpiński triangle possessing D$_{3h}$ symmetry, using <tpy-Cd$^{II}$-tpy> connectivities, in near quantitative yield through the use of structurally directed, multi-topic, 2,2':6',2"-terpyridine ligands possessing programmed structural features. NMR, ESI-MS, TWIM-MS, and TEM provided great insight into the size, shape, symmetry and the molecular structure of the assembled product. Further application of ligands possessing complementary directivity to the assembly of the higher generation structures is currently underway.

What is claimed is:

1. A method of preparing a metallotriangle-based nanomolecule comprising the steps of:
   mixing a plurality of poly-ligand monomers with a plurality of metal ions, the poly-ligand monomers being selected from the group consisting of V-, wide V-, X-, symmetric Y-, unsymmetrical Y-, K-, W-, hex-star-, penta-star-, and I-shaped monomers wherein:
   (a) the V-shaped monomers include a cyclic V-vertex group with first and second coordinating V-arms extending from the cyclic V-vertex group at 60° from one another, each of the first and second coordinating V-arms terminating in a metal-coordinating V-ligand;

(b) the wide V-shaped monomers include a cyclic wide V-vertex group with first and second coordinating wide V-arms extending from the cyclic wide V-vertex group at 120° from one another, each of the first and second coordinating wide V-arms terminating in a metal-coordinating wide V-ligand (c) the X-shaped monomers include a cyclic X-vertex group with first and second coordinating X-arms extending from the cyclic X-vertex group at 60° from one another, and opposed third and fourth coordinating X-arms extending from the cyclic X-vertex group at 60° from one another in a direction opposite to the first and second coordinating X-arms, each of the first, second, third, and fourth coordinating X-arms terminating in a metal-coordinating X-ligand;

(d) the unsymmetrical Y-shaped monomers include a cyclic unsymmetrical Y-vertex group with first and second coordinating unsymmetrical Y-arms extending from the cyclic unsymmetrical Y-vertex group at 180° from one another, and a third coordinating unsymmetrical Y-arm extending at 120° from the second coordinating unsymmetrical Y-arm, each of the first, second, and third coordinating unsymmetrical Y-arms terminating in a metal-coordinating unsymmetrical Y-ligand;

(e) the symmetric Y-shaped monomers include a cyclic symmetric Y-vertex group with first, second, and third coordinating symmetric Y-arms extending from the cyclic symmetric Y-vertex group at 120° intervals, each of the first, second, and third coordinating symmetric Y-arms terminating in a metal-coordinating symmetric Y-ligand;

(f) the K-shaped monomers include a cyclic K-vertex group with first and second coordinating K-arms extending from the cyclic K-vertex group at 180° from one another, a third coordinating K-arm extending from the cyclic K-vertex group at 60° from the first coordinating K-arm and at 120 from the second coordinating K-arm, and a fourth coordinating K-arm extending from the cyclic K-vertex group at 60° from the second coordinating K-arm and at 120 from the first coordinating K-arm, the third and fourth coordinating K-arms extending from the cyclic K-vertex group at 60 from one another, each of the first, second, third, and fourth coordinating K-arms terminating in a metal-coordinating K-ligand;

(g) the W-shaped monomers include a cyclic W-vertex group with a first coordinating W-arm and a second coordinating W-arm extending from the cyclic W-vertex group at 60° from one another, and a third coordinating W-arm extending at 60° from the second coordinating W-arm and 120° from the first coordinating W-arm, each of the first, second, and third coordinating W-arms terminating in a metal-coordinating unsymmetrical W-ligand;

(h) the hex-star-shaped monomers include a cyclic hex-star-vertex group having six coordinating hex-star-arms extending from the cyclic hex-star-vertex group at 600 intervals and each terminating in a metal-coordinating hex-star-ligand;

(i) the penta-star-shaped monomers include cyclic penta-star-vertex group having 5 coordinating penta-star-arms extending from the cyclic penta-star-vertex group at 60° intervals and each terminating in a metal-coordinating hex-star-ligand; and (j) the I-shaped monomers include a cyclic I-vertex group with first and second coordinating I-arms extending from the cyclic I-vertex group at 180° from one another, each I-arm terminating in a metal-coordinating I-ligand; and wherein:

the number and type of poly-ligand monomers and the number of metal ions are chosen and mixed in stoichiometric ratios such that, after said step of mixing, the metallotriangle-based nanomolecule self-assembles through the coordination of all of the metal coordinating V-, wide V-, X-, symmetric Y-, unsymmetrical Y-, K-, W-, hex-star-, penta-star-, and I-ligands of the plurality of poly-ligand monomers with the plurality of metal ions.

2. The method of claim 1, wherein the metal coordinating V-, wide V-, X-, symmetric Y-, unsymmetrical Y-, K-, W-, hex-star-, penta-star-, and I-ligands are selected from the group consisting of monodentate ligands, bidentate ligands, and tridentate ligands.

3. The method of claim 2, wherein each of the metal coordinating V-, wide V-, X-, symmetric Y-, unsymmetrical Y-, K-, W-, hex-star-, penta-star-, and I-ligands is a tridentate ligand.

4. The method of claim 3, wherein two of the tridentate ligands coordinate with one of the plurality of metal ions to bind 6 atoms thereto.

5. The method of claim 4, wherein the metal coordinating V-, wide V-, X-, symmetric Y-, unsymmetrical Y-, K-, W-, hex-star-, penta-star-, and I-ligands are selected from substituted 4'-attached-terpyridines, 4-substituted pyridines and aryl carboxylates.

6. The method of claim 2, wherein at least two of the metal coordinating V-, wide V-, X-, symmetric Y-, unsymmetrical Y-, K-, W-, hex-star-, penta-star-, and I-ligands are tridentate ligands and at least two of those tridentate ligands coordinate with a given metal ion.

7. The method of claim 2, wherein the metal coordinating V-, wide V-, X-, symmetric Y-, unsymmetrical Y-, K-, W-, hex-star-, penta-star-, and I-ligands are selected from pyridines, bipyridines, terpyridines, pyrroles, polypyrroles, thiophenes, polythiophenes, phosphines, polyphosphines, isoxazoles, oxazoles, pyrimidines, polypyrimidines, pyridazines, poly pyridazines, polyoxazoles, thiazoles, and polythiazoles.

8. The method of claim 2, wherein the metal coordinating V-, wide V-, X-, symmetric Y-, unsymmetrical Y-, K-, W-, hex-star-, penta-star-, and I-ligands are selected from pyridines, bipyridines, terpyridines.

9. The method of claim 1, wherein the cyclic V-, wide V-, X-, symmetric Y-, unsymmetrical Y-, K-, W-, hex-star-, penta-star-, and I-vertex groups are selected from aromatic rings with 6 atoms in the ring structure.

10. The method of claim 9, wherein the cyclic V-, wide V-, X-, symmetric Y-, unsymmetrical Y-, K-, W-, hex-star-, penta-star-, and I-vertex groups are selected from phenyl groups, naphthalene groups, polyarylenes and heteroaromatic, polyheteroaromatic, rigid cycloalkanes and cholesteric.

11. The method of claim 9, wherein the cyclic V-, wide V-, X-, symmetric Y-, unsymmetrical Y-, K-, W-, hex-star-, penta-star-, and I-vertex groups are all phenyl groups.

12. The method of claim 1, wherein the coordinating V-, wide V-, X-, symmetric Y-, unsymmetrical Y-, K-, W-, hex-star-, penta-star-, and I-arms are defined by a spacer group between a respective cyclic V-, wide V-, X-, symmetric Y-, unsymmetrical Y-, K-, W-, hex-star-, penta-star-, and I-vertex group and an associated metal coordinating V-, wide V-, X-, symmetric Y-, unsymmetrical Y-, K-, W-, hex-star-, penta-star-, and I-ligand.

13. The method of claim 12, where the at least one spacer group is selected from phenyl, biphenyl, p-terphenyl, polyarylenes and heteroaromatic, polyheteroaromatic, rigid cycloalkanes, cholesteric, and alkyne, aralkyne, diazo and polydiazo groups.

14. The method of claim 1, wherein said step of mixing includes combining the poly-ligand monomers and metal ions in a solvent.

15. The method of claim 14, where the solvent is an organic solvents.

16. The method of claim 14, where the solvent is selected from alcohols, aromatics, alkanes, alkenes, halocarbons, polar protic, polar aprotic and nonpolar liquids.

17. The method of claim 14, where the solvent is selected from from MeOH and CHCl3, CH2Cl2, toluene, benzene, and ethylene glycol.

18. The method of claim 14, where said step of mixing further includes adding counter ions, wherein said metal ions and said counter ions form metal ion-counter ion pairs soluble in said step of mixing.

19. The method of claim 1, where the metal ions have a counter ion selected from $Br^-$, $I^-$, $ClO_4^-$, $PF_6^-$, $PF_4^-$, carboxylic acids, polycarboxylic acids, triflate, bis[2,2':6', 2"]terpyridine-$(CO_2^-)_n$, and dendrimers with surface carboxylates.

20. The method of claim 1, where the poly-ligand monomers are coordinated to a metal ion with an oxidation state of +2.

21. The method of claim 1, where the metal ions are selected from the group consisting of $Fe^{+2}$, $Ru^{+2}$, $Os^{+2}$, $Ir^{+2}$, $Zn^{+2}$, $Cn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof.

22. The method of claim 1, where the metal ion is selected from the group consisting of $Zn^{+2}$, $Cn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$ and combinations thereof.

23. The method of claim 1, where the metal ion is selected from the group consisting of $Fe^{+2}$, $Ru^{+2}$, $Os^{+2}$, $Ir^{+2}$, $Zn^{+2}$, $Cd^{+2}$ and combinations thereof.

24. The method of claim 1, where sides of the metallo-triangle-based nanomolecule are defined at least in part by two of the coordinating V-, X-, Y-, K-, star-, and I-arms bound to one metal ion.

25. The method of claim 1, where the poly-ligand monomers include a functional group in addition to the ligand groups.

26. The method of claim 1, where, in said step of mixing, each poly-ligand monomer of a particular shape is identical to the other poly-ligand monomers of that shape.

* * * * *